US011701681B2

(12) United States Patent
Bush et al.

(10) Patent No.: US 11,701,681 B2
(45) Date of Patent: Jul. 18, 2023

(54) DEVICE AND METHODS FOR DEPOSITING MATERIALS ON HARD SURFACES

(71) Applicant: The Procter & Gamble Company, Cincinnati, OH (US)

(72) Inventors: Stephan Gary Bush, Liberty Township, OH (US); Ted De Castro, Newton, MA (US); Gayle Marie Frankenbach, Cincinnati, OH (US); Dana Paul Gruenbacher, Fairfield, OH (US); Kenneth Lee Morand, Maineville, OH (US); Thomas Elliot Rabe, Baltimore, MD (US); Faiz Feisal Sherman, Mason, OH (US); Nicola John Policicchio, Mason, OH (US); Philip Andrew Sawin, Cincinnati, OH (US); Jeremy Michael Carter, Union, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 426 days.

(21) Appl. No.: 17/121,826

(22) Filed: Dec. 15, 2020

(65) Prior Publication Data
US 2021/0094061 A1 Apr. 1, 2021

Related U.S. Application Data

(63) Continuation of application No. 14/968,215, filed on Dec. 14, 2015, now abandoned, which is a (Continued)

(51) Int. Cl.
*A47L 13/26* (2006.01)
*A61L 2/18* (2006.01)
(Continued)

(52) U.S. Cl.
CPC .......... *B05C 17/0052* (2013.01); *A47L 13/26* (2013.01); *A61L 2/18* (2013.01);
(Continued)

(58) Field of Classification Search
CPC .... A61L 2/18; A61L 2202/14; A61L 2202/15; A47L 13/26; B05C 17/0052;
(Continued)

(56) References Cited

U.S. PATENT DOCUMENTS 5,160,315 A 11/1992 Heinecke
5,614,310 A 3/1997 Delgado
(Continued)

FOREIGN PATENT DOCUMENTS

CN 1925778 A 3/2007
FR 2933585 B1 10/2011
(Continued)

OTHER PUBLICATIONS

All Office Actions, U.S. Appl. No. 14/855,653.
(Continued)

*Primary Examiner* — Jennifer Wecker
*Assistant Examiner* — Brady C Pilsbury
(74) *Attorney, Agent, or Firm* — Abbey A. Lopez

(57) ABSTRACT

A device and method for applying a material to a hard surface. The device has a sensor and one or more applicator nozzles. The device further includes a reservoir for containing a material to be deposited, and a CPU. The method includes providing information from the sensor about the surface to the CPU, which uses the information to identify where the material is to be deposited and/or how much to deposit.

10 Claims, 3 Drawing Sheets

Related U.S. Application Data continuation-in-part of application No. 14/736,551, filed on Jun. 11, 2015, now Pat. No. 10,188,192.

(60) Provisional application No. 62/011,846, filed on Jun. 13, 2014.

(51) Int. Cl.

| | |
|---|---|
| *B05D 1/02* | (2006.01) |
| *B05C 17/005* | (2006.01) |
| *H04N 1/62* | (2006.01) |
| *G06T 7/90* | (2017.01) |
| *C11D 3/39* | (2006.01) |
| *C11D 3/37* | (2006.01) |
| *C11D 11/00* | (2006.01) |
| *B05D 1/42* | (2006.01) |

(52) U.S. Cl.
CPC ...... *B05C 17/00503* (2013.01); *C11D 3/3723* (2013.01); *C11D 3/3902* (2013.01); *C11D 11/0023* (2013.01); *G06T 7/90* (2017.01); *H04N 1/628* (2013.01); *A61L 2202/14* (2013.01); *A61L 2202/15* (2013.01); *B05D 1/02* (2013.01); *B05D 1/42* (2013.01); *G06T 2207/10024* (2013.01)

(58) Field of Classification Search
CPC ............ B05C 17/00503; C11D 3/3902; C11D 11/0023; G06T 7/90; G06T 2207/10024; H04N 1/628; B05D 1/02; B05D 1/42
See application file for complete search history.

(56) References Cited

U.S. PATENT DOCUMENTS

| | | | |
|---|---|---|---|
| 5,674,056 | A | 10/1997 | Yamamoto |
| 6,139,829 | A | 10/2000 | Estrin |
| 6,305,046 | B1 | 10/2001 | Kingry |
| 6,312,124 | B1 | 11/2001 | Desormeaux |
| 6,325,475 | B1 | 12/2001 | Hayes |
| 6,398,358 | B1 | 6/2002 | Miyake et al. |
| 6,398,870 | B1 | 6/2002 | Kaya |
| 6,446,302 | B1 | 9/2002 | Kasper |
| 6,461,467 | B2 | 10/2002 | Blatchford |
| 6,481,515 | B1 | 11/2002 | Kirkpatrick |
| 7,166,279 | B2 | 1/2007 | Law |
| 7,890,152 | B2 | 2/2011 | Edgar |
| 8,007,062 | B2 | 8/2011 | Edgar |
| 8,027,505 | B2 | 9/2011 | Edgar et al. |
| 8,083,422 | B1 | 12/2011 | Simmons |
| 8,184,901 | B2 | 5/2012 | Edgar |
| 8,226,194 | B1 | 7/2012 | Bledsoe |
| 8,231,292 | B2 | 7/2012 | Rabe et al. |
| 9,174,445 | B1 | 11/2015 | Prati |
| 9,174,453 | B1 | 11/2015 | Dodd |
| 9,211,356 | B2 | 12/2015 | Gruenbacher |
| 9,211,980 | B1 | 12/2015 | Gruenbacher |
| 10,188,192 | B2 | 1/2019 | Rabe |
| 2004/0025368 | A1 | 2/2004 | Gerlach |
| 2004/0078278 | A1 | 4/2004 | Dauga |
| 2004/0175347 | A1 | 9/2004 | Bissett |
| 2005/0246849 | A1* | 11/2005 | Minkler .............. A47L 25/00 15/210.1 |
| 2006/0073265 | A1 | 4/2006 | Teichman et al. |
| 2006/0091238 | A1 | 5/2006 | Kutay |
| 2006/0184293 | A1 | 8/2006 | Konandreas |
| 2006/0210513 | A1 | 9/2006 | Luizzi |
| 2006/0275237 | A1 | 12/2006 | Bissett |
| 2007/0035815 | A1 | 2/2007 | Edgar |
| 2007/0049832 | A1 | 3/2007 | Edgar |
| 2007/0139508 | A1 | 6/2007 | Muyskens |
| 2007/0148120 | A1 | 6/2007 | Omura |
| 2007/0224158 | A1 | 9/2007 | Cassin |
| 2008/0194971 | A1 | 8/2008 | Edgar |
| 2008/0225068 | A1 | 9/2008 | Morino et al. |
| 2009/0025747 | A1 | 1/2009 | Edgar |
| 2009/0141112 | A1 | 6/2009 | Bergman |
| 2010/0043167 | A1 | 2/2010 | Bradbury |
| 2010/0049039 | A1 | 2/2010 | Heehler |
| 2010/0049364 | A1 | 2/2010 | Landry |
| 2010/0073440 | A1 | 3/2010 | Furukawa |
| 2010/0224210 | A1 | 9/2010 | Rabe et al. |
| 2011/0194735 | A1 | 8/2011 | Massen |
| 2011/0295229 | A1 | 12/2011 | Carlson |
| 2014/0078229 | A1 | 3/2014 | Jackson |
| 2014/0356990 | A1 | 12/2014 | Mikulan |
| 2015/0359315 | A1 | 12/2015 | Rabe |
| 2015/0359712 | A1 | 12/2015 | Rabe |
| 2015/0359714 | A1 | 12/2015 | Rabe |
| 2015/0360017 | A1 | 12/2015 | Rabe |
| 2015/0367013 | A1 | 12/2015 | Gruenbacher |
| 2015/0367014 | A1 | 12/2015 | Gruenbacher |
| 2015/0367016 | A1 | 12/2015 | Gruenbacher |
| 2015/0367356 | A1 | 12/2015 | Gruenbacher |
| 2015/0367364 | A1 | 12/2015 | Dodd |
| 2015/0367370 | A1 | 12/2015 | Dodd |
| 2015/0367373 | A1 | 12/2015 | Dodd |
| 2015/0367641 | A1 | 12/2015 | Giusti |
| 2015/0373840 | A1 | 12/2015 | Dodd |
| 2016/0096192 | A1 | 4/2016 | Bush |
| 2016/0101434 | A1 | 4/2016 | Bush |
| 2016/0102424 | A1 | 4/2016 | Bush |
| 2016/0114349 | A1 | 4/2016 | Bush |

FOREIGN PATENT DOCUMENTS

| | | |
|---|---|---|
| JP | H0725970 U | 5/1995 |
| JP | 2000210611 A | 8/2000 |
| JP | 2006297691 A | 11/2006 |
| JP | 2007044649 A | 2/2007 |
| JP | 2014114522 A | 6/2014 |
| WO | 0160274 A2 | 8/2001 |
| WO | 2006048243 A1 | 5/2006 |
| WO | 2007073917 A1 | 7/2007 |
| WO | 2007121953 A1 | 11/2007 |
| WO | 2008098234 A2 | 8/2008 |
| WO | 2008098235 A2 | 8/2008 |
| WO | 2008100878 A1 | 8/2008 |
| WO | 2008100880 A1 | 8/2008 |
| WO | 2009036876 A1 | 3/2009 |
| WO | 2009065087 A1 | 5/2009 |
| WO | 2010004526 A1 | 1/2010 |
| WO | 2010004527 A1 | 1/2010 |
| WO | 2010004528 A1 | 1/2010 |
| WO | 2010004529 A1 | 1/2010 |
| WO | 2010004530 A1 | 1/2010 |
| WO | 2010004531 A1 | 1/2010 |
| WO | 2010077703 A1 | 7/2010 |
| WO | 2010083400 A2 | 7/2010 |
| WO | 2010083405 A2 | 7/2010 |
| WO | 2015191821 A2 | 12/2015 |

OTHER PUBLICATIONS

All Office Actions, U.S. Appl. No. 14/855,662.
All Office Actions, U.S. Appl. No. 14/855,677.
All Office Actions, U.S. Appl. No. 14/950,214.
All Office Actions, U.S. Appl. No. 14/966,231.
All Office Actions, U.S. Appl. No. 14/968,177.
All Office Actions, U.S. Appl. No. 14/968,215.
All Office Actions, U.S. Appl. No. 14/968,248.
All Office Actions, U.S. Appl. No. 14/968,279.
All Office Actions; U.S. Appl. No. 14/658,280.

\* cited by examiner

DEVICE AND METHODS FOR DEPOSITING MATERIALS ON HARD SURFACES

FIELD OF THE INVENTION

This invention relates to a device and method for applying materials and/or compositions to hard surfaces. The device and method can be used to precisely apply a desired amount of the material to the desired location on the surface.

BACKGROUND OF THE INVENTION

There are many reasons to apply materials to surfaces, including to clean, protect, and/or to modify surfaces, such as, for example floors, walls, counters, cabinets, appliances, fabrics, leather and other surfaces commonly found in homes and businesses. However, current application techniques tend not to be very precise, and thus, extra material is used which or the material is applied to areas other than the intended areas. This is especially true when the application is done in the home or by other than professionals. Attempts to develop or improve devices used in the application of materials to surfaces have been made, but have generally failed to garner widespread acceptance due to their size, complexity and/or cost, especially when intended for consumer rather than commercial use.

Accordingly, there exists a need for methods and apparatuses that can precisely apply materials to surfaces. In addition there is a need for such methods and devices that can be conveniently and effectively used by non-professional consumers in locations, such as a home, school, business, hospital or other location that is not specifically designed for such precise application of the materials to the surface.

SUMMARY OF THE INVENTION

In order to address one or more of the outages of the prior art, the present invention provides the following device and methods:

A) An apparatus for applying a composition to a hard surface, the apparatus including: an applicator head comprising a microfluidic die having one or more applicator nozzles; a reservoir to hold the composition; a sensor; and a CPU; wherein the sensor is configured to sense at least a portion of the surface and provide the CPU with information about the surface, and wherein the CPU analyzes the information from the sensor to identify surface deviations, and the CPU activates the one or more applicator nozzles based on the surface deviations.

B) The apparatus of paragraph A, wherein the sensor senses color, brightness, reflectance, refractance temperature, surface height, texture, color differences, odor, variations in the surface, dirt, irregularities in the surface, bacteria or combinations thereof.

C) The apparatus of paragraphs A-B, wherein the sensor is a camera.

D) The apparatus of paragraphs A-C, wherein the microfluidic die includes a plurality of nozzles.

E) The apparatus of paragraphs A-D, wherein the microfluidic die includes a heating element or an electromechanical actuator.

F) The apparatus of paragraphs A-E, wherein the sensor is a color sensor and the sensor and the CPU is programmed to identify a $\Delta L_S$ value of plus or minus 1.5%, preferably plus or minus 1.0% even more preferably plus or minus 0.5%, of the background L.

G) The apparatus of paragraph F, wherein the predetermined $\Delta L_S$ value is greater than 3, preferably greater than 2 and more preferably greater than 1.

H) The apparatus of paragraphs A-G wherein the device is attached to a cleaning implement having a handle and a head.

I) The apparatus of paragraph H, wherein the head of the cleaning implement is configured to receive a cleaning sheet.

J) The apparatus of paragraphs A-I, wherein the CPU is configured to activates the one or more nozzles to apply the composition to the surface where the surface deviations are located.

K) The apparatus of paragraphs A-J, wherein the CPU is configured to activate the one or more nozzles to apply the composition to the surface where the surface deviations are not located.

L) The apparatus of paragraphs A-K, wherein the CPU is configured to activate the one or more nozzles in a discontinuous deposition pattern.

M) The apparatus of paragraphs A-L, wherein the CPU is configured to activate the one or more nozzles in a continuous deposition pattern.

N) The apparatus of paragraphs A-M, wherein the number and or frequency of nozzles fired can be adjusted by a user of the apparatus.

O) The apparatus of paragraphs A-N where the one or more nozzles are disposed in an array that is a linear configuration, multiple rows, off-set, sine wave, curved, circular, or saw tooth arrangements.

P) A method of depositing a composition on a hard surface, the method comprising the steps of:
identifying the hard surface onto which the composition will be deposited;
providing a device having a sensor, a reservoir for the composition, a CPU, and at least one microfluidic die comprising at least one nozzle;
locating the sensor over at least a portion of the hard surface;
activating the sensor to acquire information about the hard surface;
providing the acquired information to the CPU;
instructing the CPU to calculate the location of one or more deviations on the hard surface; and
activating the at least one nozzle to deposit the composition on the hard surface.

Q) The method of paragraph P, including the additional step of sensing the hard surface after the compostions has been deposited thereon.

R) The method of paragraphs P-Q, wherein the sensor senses the hard surface for variations in color, brightness, reflectance, refractance temperature, texture, surface height, odor, variations in the surface, dirt, irregularities in the surface, bacteria or combinations thereof and mixtures thereof.

S) The use of a device including a sensor, a CPU, a reservoir and a microfluidic die to apply a composition to a hard surface.

T) The use of paragraph S, wherein the hard surface is a surface selected from the group of: a floor, a wall, a counter top, an appliance, a grout, a tile, a window, furniture, tools, a screen, a fabric, a carpet, a floor covering, a textile, a painted surface, or combinations thereof.

BRIEF DESCRIPTION OF THE DRAWINGS

While the specification concludes with claims particularly pointing out and distinctly claiming the present invention, it is believed the same will be better understood from the following description taken in conjunction with the accompanying drawing in which:

DETAILED DESCRIPTION OF THE INVENTION

Figure 1:
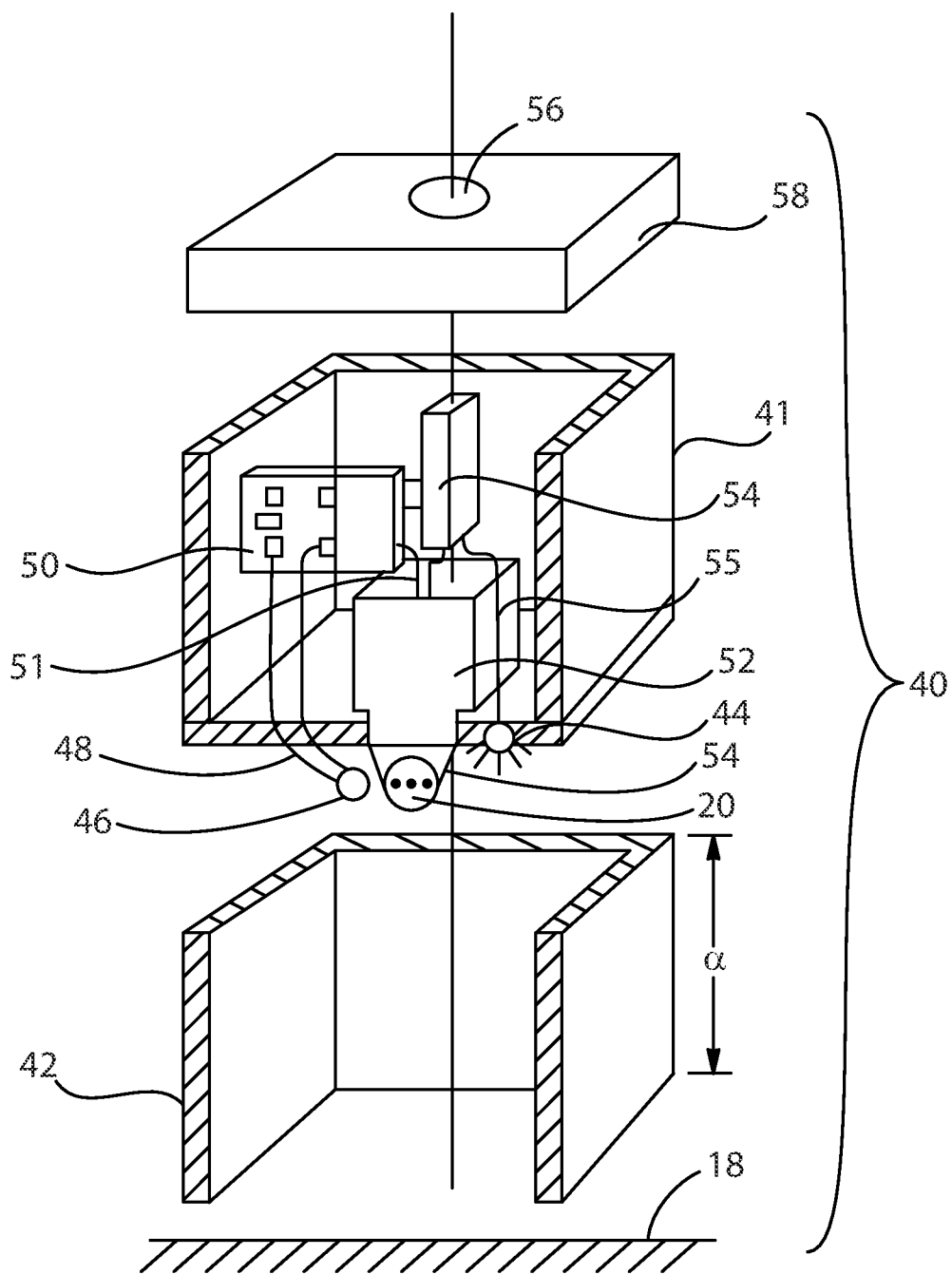
FIG. 1 is an exploded view of a hand held apparatus according to the present invention.

The present invention may be understood more readily by reference to the following detailed description of illustrative and preferred embodiments. It is to be understood that the scope of the claims is not limited to the specific compositions, methods, conditions, devices, or parameters described herein, and that the terminology used herein is not intended to be limiting of the claimed invention. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about," it will be understood that the particular values form another embodiment. All ranges are inclusive and combinable. All percentages and ratios used herein are by weight of the total composition, and all measurements made are at 25° C., unless otherwise designated.

The present apparatuses and methods, in their simplest form, are directed to the application of one or more materials or compositions to a surface. As used herein, the terms "material", "materials", "composition" and "compositions" are intended to be interchangeable and are intended to encompase any single material and any combination of materials, unless specifically restricted to any particular material or materials. The terms are not intended to limit the form of the materials, how the materials are provided or produced, or any specific characteristics of the material(s) or composition(s) unless specifically set forth and called out herein as an exception to this definition.

The present devices and methods may be used for any suitable purpose, including but not limited to one or more of the following: cleaning surfaces; coloring surfaces; filling cracks or other indentations such as scratches, dents or separations; killing mold, mildew or bacteria other living organisms; staining surfaces; deodorizing surfaces; protecting surfaces by applying one or more materials to the surface; treating surfaces with one or more materials to change a property of the surface, such as hydrophobicity; removing stains; fixing weak or broken portions of the surface; changing the surface texture; restoring the surface; applying perfume to the surface; adding material to the surface that will chemically or otherwise react (e.g. light, heat, sound, etc.) as desired to the surface or other materials that are subsequently applied to the surface or to which the surface is exposed.

Exemplary surfaces and substrates for the application of the treatment composition by the present deposition system include ceramics; grouts; plastics, manufactured surfaces such as quartz countertops; painted surfaces; glass; carpeting; tiles; wood or other natural surfaces; fibers; woven surfaces; non-woven surfaces; leather and other treated organic materials; concrete; non-porous surfaces; metals; and combinations thereof.

Method

The specific method used to apply the desired material to the target surface will vary with the particular desired use and outcome. However, certain steps will be generally applicable to various embodiments of the present invention. The following examples are intended to be non-limiting and it is fully contemplated that additional steps or alternative steps may be included when appropriate.

One non-limiting example of the method of the present invention that could be used to apply a specific material to a certain location on a surface includes the steps of taking at least one background image of at least 10 μm$^2$ of surface and then calculating the average background L value of the image on a grey scale. The background L can be calculated anywhere within the image. The background L can be the arithmetic average, median, or mean of a plurality of local Ls, which means the calculation can include all of the local Ls in the image, or a subset thereof. Further, from the same image, a localized L value is calculated for individual pixels or a group of pixels. The local L value is then compared to the background L value to identify color deviations. A color deviation is an area of the surface where the absolute value of the difference between a local L value and the background L, (this difference being defined as "$\Delta L_M$" or the measured $\Delta L$, "$\Delta$" is commonly defined as the symbol for a difference between two values) is greater than a predetermined $\Delta L_S$. The background L can be preset, or calculated by a variety of methods described below. A material can then be applied to the locations of the color deviations to reduce or increase the color deviation or otherwise apply a particular material to the specific portions of the surface desired.

The predetermined $\Delta L_S$ is the absolute value of the difference between the local L and the background L. This value, $\Delta L_S$, can be defined in absolute numbers or as a percentage. The images are taken, or converted to a standard grey scale that is known to the art. It is understood that any numerical scale that measures lightness to darkness can be considered a "grey scale". Moreover, as used herein, "grey scale" is intended to be a linear scale, or one band, or one visual attribute. For example, one "grey scale" visual attribute could be single wavelength or a narrow wavelength to define a specific visual color. Another example of one "grey scale" visual attribute could be a mix of wavelength numerical values averaged for each pixel making up the image, such as a true black, grey or white image from an RGB mixture.

It will also be understood to those skilled in the art that the background L value should not be too close to the ends of this scale. For example, if the grey scale is 0-100, with 0 being pure black and 100 being pure white, a background in the 0-10 range, or in the 90-100 range may be too light or too dark to show meaningful differences. Accordingly, one can adjust the background lighting, or the gain on the camera taking the image, to move the background L closer to the middle of the scale. In this example, a background L of 50 would work well, with a background L in the range of 10-90 or 20-80 being even more preferred.

The most common grey scale is 0-255 (no units) and other examples include 0-1024 and 0-4096. For a grey scale of 0-255, the difference between grey scale steps is at least 1/255. In this example it would be desirable to use camera and lighting settings that provide a background L value between 60 and 210. Using the 0-255 gray scale the $\Delta L_S$ is preferably at least 0.5, at least 1 or at least 1.5 to initiate deposition of the material on the surface. Likewise, $\Delta L_S$ can be measured as a percentage, for example, a numerical $\Delta L_S$ of 2.6 is approximately equal to 1.0% of a 255 grey scale. Thus, $\Delta L_S$ may be plus or minus 0.25%, plus or minus 0.5%, or plus or minus 0.75%, of the grayscale.

Images may be taken in sequence or preferably continuously. Higher speed cameras, cameras that capture greater than 4 frames per second, greater 100 frames per second, greater than 200 frames per second, and even greater than 600 frames per second may be desired for certain applications. The images are preferably either taken in a grey scale or converted to a grey scale. The grey scale can have any range, for example, 0-255, no units. This corresponds approximately to a refresh rate of 0.2 seconds or faster. Consistent with the camera, it may be desirable to choose a CPU that can process the images at a rate that is at least that of the rate the images are captured.

There is no technical difference between an image used for background L values and those used for local L values, the difference is in the analysis of the image. Hence, the images are continually sent to the CPU, that is, the processing unit, to calculate the L values, and $\Delta L_M$ values. By "sent" it is understood, that preferably at least 4 bits of data per pixel are transferred for each image, and preferably, this 4 bit (or more) packet of data is used in the calculation of each local L value. It is understood, that the background L can be calculated once in a treatment period and that value reused throughout the treatment period. Or it can be continually recalculated as long as the treatment process goes on. Moreover, there can be pre-programmed triggers to initiate a recalculation of the background L. Also, the background L may be retrieved from the CPU memory to be used for the current background L. For example, if an extended period of time elapses and no skin deviations are found, or if skin deviations are being found too frequently, a new background L might automatically be calculated. Likewise, $\Delta L_S$ can be a set value that remains constant throughout the treatment cycle or it too can vary. $\Delta L_S$ can be reset during the treatment cycle for any of a variety of reasons. If too many nozzles are firing too frequently, the $\Delta L_S$ can be adjusted to lower the intensity of the nozzle firing. Similarly, if the nozzles are firing too infrequently, $\Delta L_S$ can be adjusted in the opposite direction to increase the sensitivity of skin deviation detection. Those skilled in the art will appreciate that modifying $\Delta L_S$ during treatment is a matter of programming the CPU to or with a desired algorithm.

When the $\Delta L_M$ exceeds the predetermined value, a material may be applied to the deviation. Specifically, one or more of the nozzles which dispense the composition is fired in the area of the skin deviation. The composition may be applied to surface in a continuous or discontinuous deposition pattern. The composition or materials can be applied to the surface by scanning and applying at the same time and/or while making multiple passes over the surface. Several advantages result from using multiple pass application. The process for multiple pass applications is to make a partial application of the composition, then to scan again the area of surface that has received the partial application. A further application of compositions can be made, and still further multiple pass scanning and applications can be made to approach a specific goal. Thus, the consumer can select the end point of the application, thus tailoring the application time to individual needs and preferences.

The method described above can also be used to identify surface irregularities such as cracks, dents, openings, imperfections, etc. Once identified, the areas of deviation can have a material applied thereto to provide the desired end result. For example, a crack in a tile may be filled, caulk may be applied to an opening between construction materials, grout may be applied to the space between tiles, wood filler may be applied to a dent in a wood floor or a material may be applied to a scratch or dent in a painted surface to fill, repair, and/or hide the imperfection. In other situations, the method may be used to identify stains in fabrics and to apply cleaning agents or hueing dyes. Still other uses for the method can be to apply sealing materials, pigments, antibacterial agents, perfumes, masking agents, or any other desired material to a specific portion of a surface.

Device

A non-limiting example of the device of the present invention is a hand-held device that includes a sensor and an applicator. The applicator may include one or more nozzles and a reservoir for containing the composition to be applied to the desired surface. The device may also include an optional illumination source and a CPU. The illumination source can illuminate the surface to be sensed and the sensor can sense information from the surface that is used to determine how much material is applied to the surface and where. In a simple example, the device may include a sensor that records an image of the surface, a CPU to analyze the image to determine where and how much material is to be deposited on the surface and an applicator to apply the desired amount of the material to the desired location on the surface.

The sensor may used to sense any number of attributes of the surface to which the material is to be applied. The sensor may be, for example, a camera that takes black and white or color images, a spectrophotometer or similar devices that are sensitive to electromagnetic energy wavelengths. The sensor output may be used to calculate the localized L value of individual pixels or groups of pixels of the surface. The CPU can then compare the local L value to the background L value to identify surface deviations where the difference between the two L values is greater than a predetermined value. The sensor readings may include, but are not limited to values selected from the group of color, brightness, reflectance, refractance temperature, texture, depth, width, length, odor, and mixtures thereof.

The central processing unit ("CPU") of the device can be any of a variety of commercially available devices. In its simplest form, the CPU is a single programmable chip like those found in consumer electronic devices such as a lap top computer, a cell phone, an electric razor and the like. Those skilled in the art will know of a variety of commercially available chips and other processors suitable for use with this invention. CPU may include Application Specific Integrated Circuit (ASIC), controller, Field Programmable Gate Array (FPGA), integrated circuit, microcontroller, microprocessor, processor, and the like. The CPU may also include memory functionality, either internal to the CPU as cache memory, for example Random Access Memory (RAM), Static Random Access Memory (SRAM) and the like or external to the CPU for example as Dynamic Random-Access Memory (DRAM), Read Only Memory (ROM), Static RAM, Flash Memory (e.g., Compact Flash or SmartMedia cards), disk drives, Solid State Disk Drives (SSD) or even Internet Cloud storage. While it is anticipated that a remote CPU, either tethered to the device, or which communicates wirelessly, can be used to accomplish the methods of the present invention, a local CPU within the device is exemplified herein. The appropriate size and speed of the CPU may be determined based on the particular desired uses of the device.

The applicator of the device may be any applicator that can provide for precision delivery of the material to the surface. For example, microfluidic dies may be used alone or in combination with other technologies. The term "microfluidic die", as used herein means a die comprising a fluid injection system made using a semiconductor micro fabrication process such as thin film deposition, passivation, etching, spinning, sputtering, masking, epitaxy growth, wafer/wafer bonding, micro thin-film lamination, curing, dicing, etc. These processes are known in the art to make MEMs devices. Microfluidic dies may be made from silicon, glass, or a mixture thereof. The microfluidic die comprises a plurality of microfluidic chambers, each comprising a corresponding actuation element: a heating element or an electromechanical actuator. In this way, the microfluidic die's fluid injection system may be micro thermal nucleation (e.g. via heating element) or micro mechanical actuation (e.g. via thin film piezoelectric or ultrasonics). One type of microfluidic die suitable for the microfluidic delivery system of the present invention is an integrated membrane of nozzles obtained via MEMs technology as described in U.S. 2010/0154790, assigned to STMicroelectronics S.R.I., Geneva, Switzerland. In the case of thin film piezo, the piezoelectric material is typically applied via spinning and/or sputtering processes. The semiconductor micro fabrication process allows one to simultaneously make one or thousands of MEMS devices in one batch process (a batch process comprises of multiple mask layers). The microfluidic delivery member includes a die having a fluid chamber with an inlet and an outlet.

While microfluidic dies and inkjet-like cartridges are shown and exemplified herein, compositions may be applied with other "flow control" devices or non-drop control devices. Flow control devices typically are characterized as "drop control devices" where individual droplets of the substance are controlled. Examples of drop control include "fine flow control" where the flow of the substance is precisely controlled to deliver droplets as desired and "inkjet technologies." An older inkjet technology includes supplying a continuous flow of charged droplets past electrostatic deflector plates which are alternately charged so that the plates either permit a droplet to pass or deflect to a gutter. This technique was the original design basis for inkjet printers. Other inkjet technologies include "drop on demand" such as thermal devices provided by Hewlett Packard, and piezoelectric devices such as provided by Epson and other printer manufacturers. Drop on demand technology may also be combined with charging the droplets.

Other suitable devices for depositing the materials include, but are not limited to, piezo electric drop control devices and other micro electromechanical systems. Yet other spray devices, including electrostatic spray devices, that are non-drop control devices may be used, but since they tend not to provide the desired control of the material to be deposited they may not be suitable for all applications of the technology. However, in certain circumstances, they may be useful to be used alone or in combination with other technologies. For example, such technologies can provide some "randomness" to the deposition of the material, which may be desired in order to produce a smooth application over a relatively large area. However, because the general intent of the present invention is to allow a user to provide very specific control of the amount and/or placement of the compositions on the target surface, these technologies may not be suitable for every contemplated use of the present invention.

In devices including one or more nozzles, the composition may be dispensed by "firing" one or more of the nozzles when the nozzles are located adjacent the surface deviation or other identified region for application of the composition. By "firing" it is meant that the composition is forced through the nozzle. The composition may be applied to surface in a continuous or discontinuous deposition pattern via one or more nozzles. Where multiple nozzles are used, they may be disposed in an array. The "array" can be a linear configuration, multiple rows, off-set, sine wave, curved, circular, saw tooth arrangements, or any other desired arrangement of the nozzles. The number and location of nozzles as with the frequency of their firing can be static or can be adjustable. Those skilled in the printing arts will appreciate the various configurations of nozzle arrays that are possible for use in the methods and apparatuses disclosed herein.

Firing intensity curves can be programmed into the CPU to adjust the firing rate of nozzles. For example, if $\Delta L_M$ is equal to or slightly greater than $\Delta L_S$, then the adjacent nozzle is fired 1 time. If $\Delta L_M$ increases to $2*\Delta L_S$, then the adjacent nozzle is fired 25 times. If the $\Delta L_M$ is $3*\Delta L_S$, then the adjacent nozzle is fired 100 times. This non-limiting example is intended to show how the size of the $\Delta L_M$ with respect to the $\Delta L_S$ can determine the amount, and hence, the intensity of the firing of the nozzles. Those skilled in the art will appreciate that plotting a firing intensity curve using 2, 3 or more data points, and then programming that firing intensity curve into the CPU are known techniques.

Exemplary equipment that could be useful in constructing an apparatus of the present invention is described in the following published patent applications: WO 2008/098234 A2, Handheld Apparatus and Method for the Automated Application of Cosmetics and Other Surfaces, filed 11 Feb. 2007; WO 2008/100878 A1, System and Method for Applying a Treatment composition to Change a Person's Appearance Based on a Digital Image, filed 12 February, 2007; WO 2008/098235 A2, System and Method for Providing Simulated Images Through Cosmetic Monitoring, first filed 11 February, 2007; WO 2008/100880 A1, System and Method for Applying Agent Electrostatically to Human Skin, filed 12 February, 2007; US 2007/0049832 A1, System and Method for Medical Monitoring and Treatment Through Cosmetic Monitoring and Treatment, filed 12 Aug. 2005; and US 2007/0035815 A1, System and Method for Applying a Treatment composition to Improve the Visual Attractiveness of Human Skin, filed 12 Aug. 2005; U.S. Ser. No. 14/736,551 entitled Apparatus And Methods For Modifying Keratinous Surfaces, filed Jun. 11, 2015.

Compositions

The present invention may utilize any desired composition, material or mixture of compositions or materials. For example, the composition may include inks, dyes, pigments, adhesives, curable compositions, optically activated compounds, metal oxides, bleaching agents, texture reducing polymers, silicones, stains, paints, surfactants, cleaners, malodor reducing agents, lubricants, fillers, perfumes, scents, polymers, polymeric additives, particles, optical modifiers, optical matchers, and other actives such as antibacterial and antimicrobials, and combinations of these or other materials, some of which are further described herein.

The composition can be delivered in a variety of product forms including, but not limited to, a cream, a lotion, a gel, a foam, a paste, particles, liquid, mixture, or a serum and may be applied as a single phase or material or as multiple phases or multiple materials. Additionally, the composition can include for stabilizers or other processing and/or preservative ingredients.

Additionally, the compositions can be delivered alone or in the presence of a carrier. The carrier, if any, can be in a wide variety of forms. Non-limiting examples include simple solutions (water or oil based), emulsions, and solid forms (gels, sticks, flowable solids, wax, amorphous materials). In certain embodiments, the carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof. For example, emulsion carriers can include, but are not limited to, continuous water phase emulsions such as silicone-in-water, oil-in-water, and water-in-oil-in-water emulsion; and continuous oil phase emulsions such as water-in-oil and water-in-silicone emulsions, and oil-in-water-in-silicone emulsions. Other carriers or chassis include humectants, one example of which is a polyhydric alcohol. Exemplary polyhydric alcohols include polyalkylene glycols and alkylene polyols and their derivatives, including propylene glycol, dipropylene glycol, polypropylene glycol, polyethylene glycol and derivatives thereof; sorbitol; hydroxypropyl sorbitol; erythritol; threitol; pentaerythritol; xylitol; glucitol; mannitol; butylene glycol (e.g., 1,3-butylene glycol); pentylene glycol; hexane triol (e.g., 1,2,6-hexanetriol); glycerin; ethoxylated glycerine; and propoxylated glycerine. Yet other humectants include sodium 2-pyrrolidone-5-carboxylate, guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; sodium pyroglutamate, water-soluble glyceryl poly(meth)acrylate lubricants (such as Hispagel) and mixtures thereof.

Non-Limiting Examples

FIG. 1 shows an exploded view of an example of a handheld apparatus or device 40 according to the present invention. Apparatus 40 is shown directly above surface 18, separated by physical spacer 42. Physical spacer 42 may be a portion of the device 40 or may be a separate piece that may be used to help the user locate the device above the surface 18. As shown, the spacer 18 has a set, predetermined height a such that when it contacts surface 18, but it is contemplated that the spacer may be adjustable or that different spacers could be used for different purposes. The spacer 18 helps the user maintain the mechanical and electrical elements above the surface are all at a known distance from the surface.

The mechanical and electrical elements associated with apparatus 40 include, but may not be limited to, light 44, image capture device 46, nozzle array 20 (which is shown embedded on cartridge die 54) which is shown attached to cartridge 52. Preferably, all of these elements are enclosed within optional apparatus housing 41, although other embodiments are contemplated wherein one or more of the elements are located outside housing 41. Light 44 illuminates an area of the surface 18 such that the image capture device 46 has relatively constant illumination. In situations where background lighting could affect the image capture, the spacer 42 prevents background light in and/or the illumination from light 44 to escape. Generally, however, small deviations in illumination can be corrected for provided light 44 provides a relatively constant background illumination. Light 44 can be a light emitting diode (LED), incandescent light, neon bulb based or any other commercially available source of illumination. Light 44 can have constant illumination or adjustable illumination. For example, an adjustable light source might be useful if the background illumination is excessively bright or dark.

Image capture device 46 can be any of a variety of commercially available devices such as a simple camera or a digital cmos camera chip. Image capture device 46 takes a picture of surface 18 and sends it to processor 50 via image capture line 48 for analysis. Alternatively or additionally, the device 40 may include sensors other than the image capture device. For example, it may be desirable to sense the texture of a surface, the color of a surface, materials on a surface, the friction of a surface or other physical and/or aesthetic features. Sensors available for sensing any desired property of the surface can be used with the device 40. The information sensed by the sensor can be provided to the processor 50.

Processor 50 is generally referred to as a central processing unit, or CPU, which may comprise a simple circuit board, a more complex computer, or the like and may include memory functionality. Those skilled in the art will appreciate that a CPU can be any of wide variety of commercially available programmable devices.

If an image capture device 46 is used, the image may be analyzed for local L values, background L values, both or other values consistent with the particular use of the device 40. Grey scale conversion occurs within the analytical processing capabilities of processor 50. The comparison of background L to local L to determine the $\Delta L_M$ occurs within processor 50, which can be a commercially available programmable chip, or other commercially available processing units. The results of the image analysis, when compared to criteria pre-programmed into the processor, may result in a desired application of a material to the surface. In such a case, for example when the calculate $\Delta L_M$ exceeds the pre-determined $\Delta L_S$, a signal is sent from processor 50 to cartridge 52, via cartridge line 51, to fire one or more of the nozzles in nozzle array 20.

Power for cartridge 52, light 44, image capture device 46, processor 50, and other mechanical and electrical elements that might be present is supplied by power element 54 via multiple power lines 55. Power element 54 can be turned off and on, which in turn turns apparatus 40 off and on, via power switch 56 which can be located anywhere on apparatus 40, but is shown here on apparatus cover 58. Power element 54 may include energy storage functionality via a battery, a rechargeable battery, an electrochemical capacitor, a double-layer capacitor, a supercapacitor or a hybrid battery-capacitor system.

Figure 2:
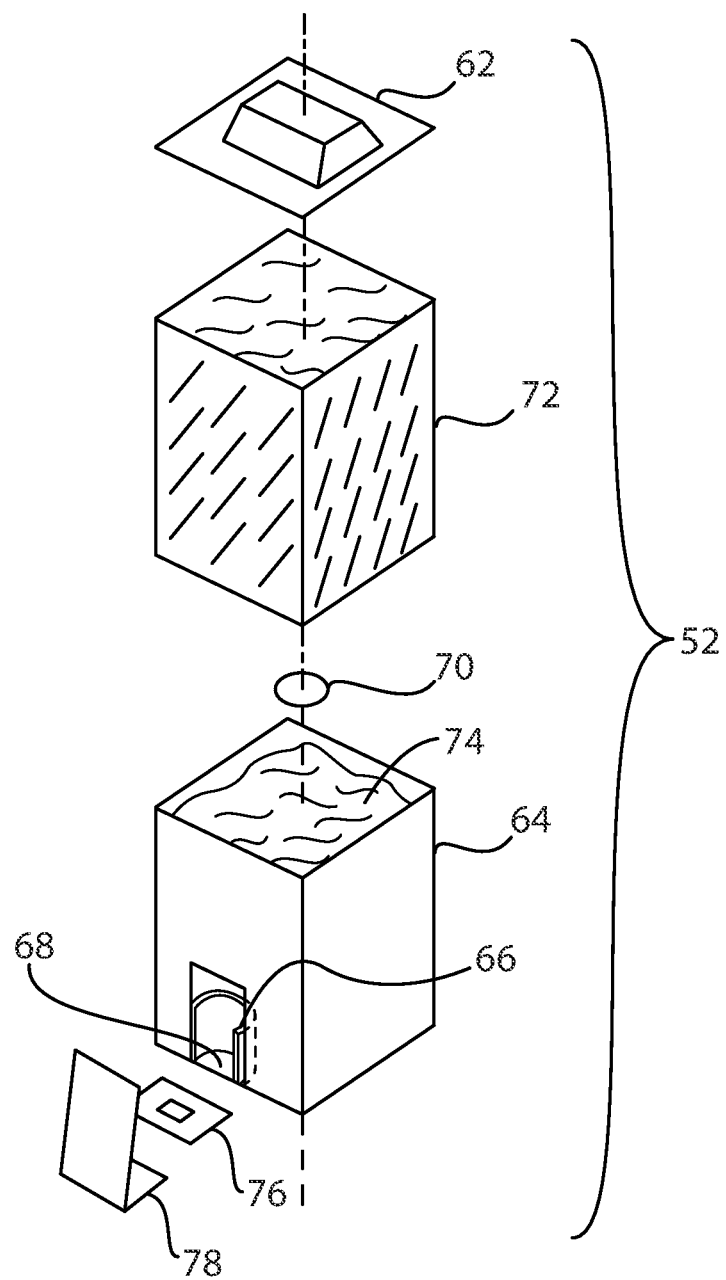
FIG. 2 is an exploded view of a cartridge that may be used with the device of the present invention.

Turning now to FIG. 2, an exploded view of cartridge 52 is shown. The cartridge 52 includes cartridge cap 62 and cartridge body 64. Body 64 includes standpipe 66 which is typically enclosed within body 66 and defines nozzle outlet 68. Optional filter 70 helps keep excessively large particles, and other debris out of the nozzle array 76. Filter 70 and nozzle array 76 are shown on opposite sides of nozzle outlet 68, although other configurations are contemplated. Composition 74 partially fills cartridge body 64. Core 72 fills cartridge 64 and helps to regulate back pressure of the composition 74. Core 72 may be a sponge, foam, fibrous material, paper or any other material suitable for the desired operation. Back pressure can be regulated via bladders and/or other methods known to the art. The core 72 shown is just one example of how to help regulate flow of the composition 74 to standpipe 66 through filter 70 and into nozzle array 76. Connector 78 provides the electrical power and signal to nozzle array 76. Composition 74 may be ejected from the cartridge 52 by piezoelectric means, thermal means, mechanical pumping means or a combination of these or others know and/or set forth herein.

Figure 3:
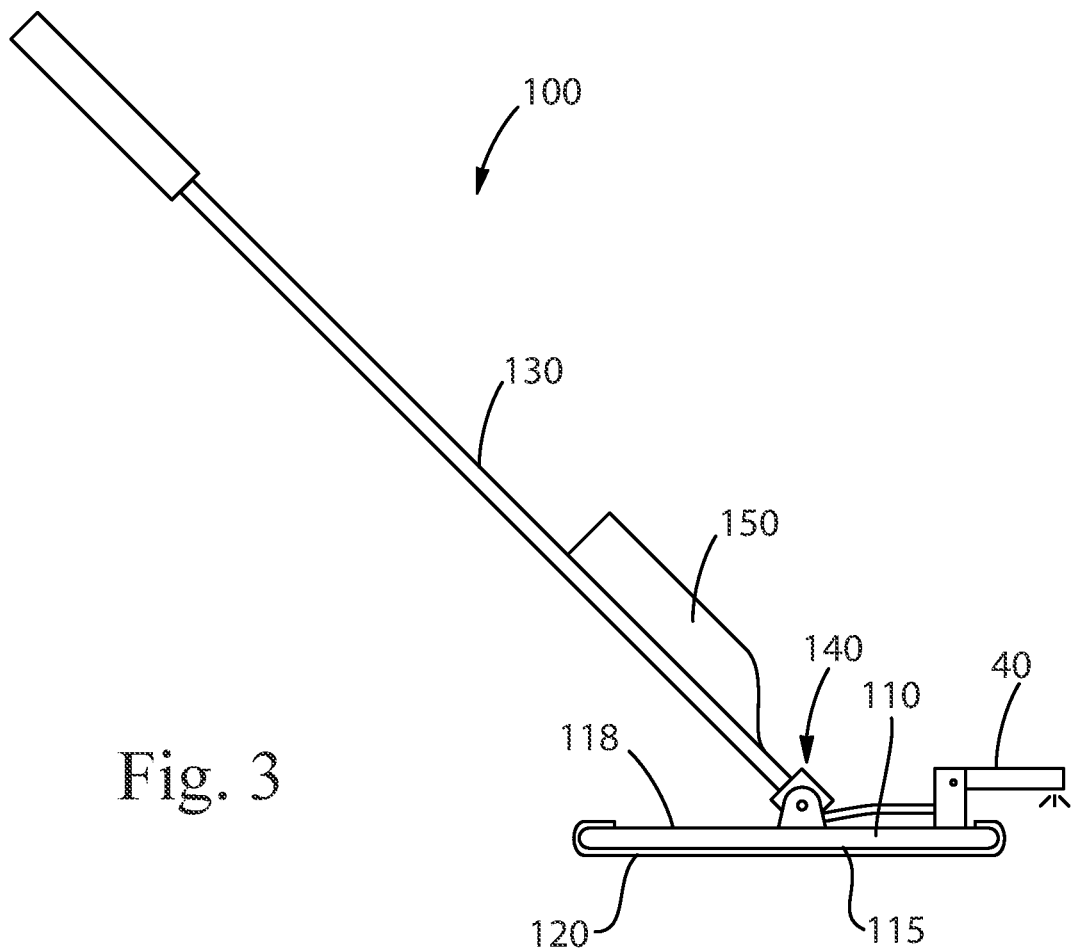
FIG. 3 is a side view of an example of the device of the present invention mounted on a cleaning implement.

The device or apparatus of the present invention may be configured to be held in the hand of a user or can be mounted to a structure that allows the user to more easily move the apparatus across the surface to be modified, an example of which is shown in FIG. 3. In either case, during use, the consumer can simply move the apparatus across the surface to be treated. Optionally, the device can be configured in a stationary structure wherein the consumer moves the surface to be treated across the device. Embodiments are also contemplated where more than one device is used. In such configurations, similar devices can be used in parallel or in series. In other configurations, different devices can be combined together.

If the device 40 according to the present invention is used with a cleaning implement, the cleaning implement may include any known structure. For example, the cleaning implement may be a wet or dry mop, a vacuum, a squeegee or any other implement. One exemplary embodiment is shown in FIG. 3. The implement 100 includes a plastic head 110 for holding the cleaning sheet 120 and an elongate handle 130 articulably connected thereto. The handle 130 may comprise a metal or plastic tube or solid rod. The head 110 may have a downwardly facing surface 115, to which the sheet 120 may be attached or against which the sheet 120 may be located. The downwardly facing surface 115 may be generally flat, or slightly convex. The head 120 may further have an upwardly facing surface 118. As shown in FIG. 3, the sheet 120 may be attached to the upwardly facing surface 118 and wrap around at least a portion of the downwardly facing surface 115 of the head 110. The upwardly facing surface 118 may have a universal joint 140 or the like to facilitate connection of the elongate handle 130 to the head 110. The device 40 of the present invention may be mounted to the head 110 of the implement 100, the handle 130 or any other portion of the implement 100.

A hook and loop system may be used to attach the cleaning sheet 120 directly to the bottom of the head 110. Alternatively, the upwardly facing surface 118 may further comprise a mechanism, such as resilient grippers, for removably attaching the cleaning sheet 120 to the implement 100. If grippers are used with the cleaning implement, the grippers may be made according to commonly assigned U.S. Pat. Nos. 6,305,046; 6,484,346; 6,651,290 and/or D487,173.

The cleaning implement 100 may further comprise a reservoir 150 for storage of a cleaning solution or other composition. The reservoir 150 may be replaced when the cleaning solution is depleted and/or refilled as desired. The reservoir 150 may be disposed on the head or the handle of the cleaning implement. The neck of the reservoir may be offset per commonly assigned U.S. Pat. No. 6,390,335. The cleaning solution contained therein may be made according to the teachings of commonly assigned U.S. Pat. No. 6,814,088.

If a cleaning sheet 120 is used, it may comprise a nonwoven. The nonwoven may be synthetic and/or have cellulosic fibers therein. The synthetic fibers may comprise carded, staple, wet laid, air laid and/or spunbond fibers. The cleaning sheet 120 may comprise layers, to provide for absorption and storage of cleaning fluid deposited on the target surface. If desired, the cleaning sheet 120 may comprise absorbent gelling materials to increase the absorbent capacity of the cleaning sheet. The absorbent gelling materials may be distributed within the cleaning sheet in such a manner to avoid rapid absorbency and absorb fluids slowly, to provide for the most effective use of the cleaning sheet.

The cleaning sheet 120 may comprise plural layers disposed in a laminate. The lowest, or downwardly facing outer layer, may comprise apertures to allow for absorption of cleaning solution therethrough and to promote the scrubbing of the target surface. Intermediate layers may provide for storage of the liquids, and may comprise the absorbent gelling materials. The cleaning sheet 120 may have an absorbent capacity of at least 10, 15, or 20 grams of cleaning solution per gram of dry cleaning sheet, as set forth in commonly assigned U.S. Pat. Nos. 6,003,191 and 6,601,261. The top, or upwardly facing outer layer, maybe liquid impervious in order to minimize loss of absorbed fluids. The top layer may further provide for releasable attachment of the cleaning sheet to a cleaning implement. The top layer may be made of a polyolefinic film, such as LDPE.

The device of the present invention may also be or be associated with a duster or other surface cleaning device. In one such embodiment, the device may include sole plate with a permanent cleaning surface and a removable/replaceable cleaning surface. The replaceable cleaning surface may comprise a pad. The device may also include a replaceable, on-board supply of cleaning solution. The pad/cleaning solution may be replaced when depleted and replaced with a new pad/cleaning solution or may simply be replaced with a new pact/cleaning solution which may be more suitable for a particular cleaning task.

In use, application times will vary based on the size of the application area and the precision and amount of the material that is desired to be applied. For example, a user may wish to simply touch up a small scratch on a surface and the application might take just a few seconds or minutes. Alternatively, a user may wish to restore the look of an entire counter top. This type of application could take minutes or hours. Accordingly, the consumer will have tremendous control over how and for what the device and process is used. Further, to ensure the nozzles do not clog, it may be desirable to fire nozzles periodically to keep them clean or clear.

Exemplary Uses

Color:

The method and device of the present invention may be used to provide and/or modify the color, reflectance or other aesthetic features of a surface. For example, it may be desirable to add color to a portion of a surface. It may be desirable to do so in order to change the color of that portion of the surface, restore the original color of the surface, mask a color or other feature of a surface, such as, for example, a defect or discoloration. As such, it may be desirable to provide a composition or mixture of compositions that include color, hue, pigment or other materials. Examples of such compostions include, but are not limited to inks, dyes, metal oxides and pigments (collectively referred to herein as "colorants"). Colorants may include inorganic or organic pigments and powders. Organic pigments can include natural colorants and synthetic monomeric and polymeric colorants. Organic pigments include various aromatic types such as azo, indigoid, triphenylmethane, anthraquinone, and xanthine dyes which are designated as D&C and FD&C blues, browns, greens, oranges, reds, yellows, etc. Organic pigments may consist of insoluble metallic salts of certified color additives, referred to as the Lakes. Inorganic pigments include iron oxides, ferric ammonium ferrocyanide, manganese violet, ultramarines, chromium, chromium hydroxide colors, and mixtures thereof. The pigments may be coated with one or more ingredients that cause the pigments to have desired characteristics, such as hydrophilicity or hydrophobicity. Exemplary coating materials include silicones, lecithin, amino acids, phospholipids, inorganic and organic oils, polyethylene, and other polymeric materials. Exemplary silicone treated pigments as disclosed in U.S. Pat. No. 5,143,722. Inorganic white or uncolored pigments include $TiO_2$, ZnO, $ZrO_2$, hollow spheres or semiconductor quantum dots, which are commercially available from a number of sources. Other suitable colorants are identified in U.S. Pat. No. 7,166,279.

Adhesives:

Adhesives can be applied to surfaces with the device and method of the present invention. It may be desirable to apply the adhesive to the surface alone or to apply the adhesive with or in anticipation of another material that will stick to the adhesive. Examples of adhesives include those described, for example, in U.S. Pat. No. 6,461,467, issued to Blatchford, et al., filed on Apr. 23, 2001; U.S. Pat. No. 5,614,310, issued to Delgado, et al., filed on Nov. 4, 1994; and U.S. Pat. No. 5,160,315, issued to Heinecke et al., filed on Apr. 5, 1991.

As noted above, after an adhesive is applied to a surface, a second composition may be applied to the surface and/or adhesive. In one embodiment, the second material that is not adhered to the adhesive can be removed leaving behind a selective, micro application of the second material to the surface.

Activatable Materials:

Compositions that cure or are otherwise activated upon exposure to certain wavelengths of energy, infrared light or UV for example, are know to the art and can be applied by the device and method of the present invention. For example, a light curable composition may be selectively applied to the surface and then cured by exposing the surface to the curing energy source. The entire surface can be exposed to the activation source or the exposure can be done by the device at the same time as the application and selectively to the material that is applied to the surface.

An example of an activatable material is one that includes optically-activated particles. Such materials are sometimes referred to a "interference pigments". They often include a plurality of substrate particles selected from the group consisting of nylons, acrylics, polyesters, other plastic polymers, natural materials, regenerated cellulose, metals, hollow spheres, semiconductor quantum dots and minerals; an optical brightener chemically bonded to each of the plurality of substrate particles to form integral units in the form of optically-activated particles for diffusing light. These materials can help to reduce the visual perception of imperfections, including dents, scratches, cracks, and discolorations. The optically-activated particles may be encapsulated with a UV transparent coating to increase the diffusion of light to further reduce the visual perception of the imperfections. Such encapsulated optically-activated particles are able to absorb ultraviolet radiation and emit visible light as well as scatter and absorb light in a diffuse manner in order to reduce the visual perception of the imperfections.

Fillers:

The method and device of the present invention may be used to fill depressions in surfaces such as cracks, dents, slits, openings and the like. For example, the device and method may be used to fill cracks in wood floors, tiles, lenses, countertops, pavement, walls and other hard surfaces. Additionally, the method and device may be used to fill crack or the like in flexible surfaces such as leather, plastics, fabrics, films, foils and the like. Examples of compositions that can be used for such purposes include the aqueous oil-in-water emulsion scratch cover composition for finished wood disclosed in WO 1994010237 A1; the compositions for fixing wood floor scratches disclosed in US 2011/189387; the curable filler composition for veneer repair disclosed in US 2008/0152876; the compositions in U.S. Pat. No. 8,128,718; the solid polishing materials disclosed in U.S. Pat. No. 5,334,335; those set froth in U.S. Pat. Nos. 5,082,691; 5,821,291 and WO 9607706. Other fillers include urethane prepolymer with an isocyanate group at the terminal and obtained by reacting polyole including polytetramethyleneglycol and/or modified polytetramethyleneglycol with a polyisocyanate compound as described in more detail in JP 5106801.

In these types of uses, it may be desirable for the device to sense changes in the tropography of the surface in order to determine where to apply the material. However, it would also be possible to use color changes, such as the L value changes set forth herein to determine where to apply the composition and how much, etc. It may even be desirable to combine topography sensing with color sensing to ensure the target area is accurately identified and/or appropriately modified by the applied composition.

Hard Surface Cleaners:

The method and device of the present invention may be used to provide precice application of cleaning compositions to hard surfaces. For example, it may be desirable to clean a particular spot on a surface, such as a floor, wall, tile, caulk, grout, window, cupboard, sink, shower, shower plastified curtain, wash basin, toilet, fixture or fitting and the like made of different materials like ceramic, vinyl, no-wax vinyl, linoleum, melamine, glass, steel, kitchen work surfaces, any plastics, plastified wood, metal or any painted or varnished or sealed surface and the like. One specific application would be the cleaning or removal of mold or mildew from grout lines. Household hard surfaces also include household appliances including, but not limited to refrigerators, freezers, washing machines, automatic dryers, ovens, microwave ovens, dishwashers and so on. Such hard surfaces may be found both in private households as well as in commercial, institutional and industrial environments.

Hard surface cleaning compositions are used for cleaning and treating hard surfaces. Preferably, the hard surface cleaning composition is formulated to be an "all purpose" hard surface cleaning composition. That is, the hard surface cleaning composition is formulated to be suitable for cleaning as many different kinds of surfaces as possible. Hard surface cleaning compositions are typically diluted before use in a bucket before being applied to the surface being cleaned using a mop, sponge, cloth or similar device. Especially when cleaning particularly dirty floors, film and streak residues may be left which result in poor shine, and an impression that the surface is not yet sufficiently clean. In addition, such floors, washed with diluted hard surface cleaning compositions, tend to be slippery with a resultant increase in the risk of falls and similar accidents, until dry. Hence, the present invention can not only reduce the amount of cleaner needed, but also reduce some of the undesirable aspects of cleaning a hard surface by precisely delivering the cleaning agent to the desired location.

Hard surface cleaner compositions may be in liquid form and are often aqueous compositions. As is common today, hard surface cleaners generally comprise from 30% to 99.5% by weight of the total composition of water. However, the present invention may allow for higher concentrations of cleaning actives as the compositions are contained in the device until used and then applied very precisely to the desired location.

The hard surface cleaner may be acidic or basic. The composition may have a pH from about 2 to about 14, from about 2 to about 10, from about 2 to about 9.5, or from about 2.1 to about 8, as is measured at 25° C.

The composition may have any suitable viscosity. In certain embodiments, the composition may be "water-like" having a viscosity that is close to that of water. The composition may have a viscosity of up to about 50 cps, from about 0 cps to about 30 cps, from about 0 cps to about 20 cps, or from about 0 cps to about 10 cps at 60 rpm and 20° C., when measured with a Brookfield digital viscometer model DV II, with spindle 2. The composition may also be thickened, as desired. Thus, the composition may have a viscosity of from about 50 cps to about 5000 cps, from about 50 cps to about 2000 cps, from about 50 cps to about 1000 cps, or from about 50 cps to about 500 cps at 20 $s^{-1}$ and 20° C., when measured with a Rheometer, model AR 1000 (Supplied by TA Instruments) with a 4 cm conic spindle in stainless steel, 2° angle (linear increment from 0.1 to 100 $sec^{-1}$ in maximum 8 minutes). Preferably, the thickened composition according to the embodiment is a shear-thinning composition. The thickened composition herein preferably comprises a thickener, more preferably a polysaccharide polymer thickener, still more preferably a gum-type polysaccharide polymer thickener, and preferably a Xanthan gum thickener.

The composition may comprise a surfactant or a mixture thereof as one preferred, but optional ingredient to provide cleaning capabilities. Suitable surfactants are selected from the group consisting of an anionic surfactant or a mixture thereof; a nonionic surfactant or a mixture thereof; an amphoteric surfactant or a mixture thereof; a zwitterionic surfactant or a mixture thereof; and mixtures thereof. The composition may comprise from about 1% to about 60%, from about 5% to about 30%, or from about 10% to about 25% by weight of the total composition of a surfactant.

Suitable nonionic surfactants for use in the composition are alkoxylated alcohol nonionic surfactants, which can be readily made by condensation processes which are well-known in the art. However, a great variety of such alkoxylated alcohols, especially ethoxylated and/or propoxylated alcohols, are conveniently commercially available. Surfactant catalogs are available which list a number of surfactants, including nonionics. Preferred alkoxylated alcohols for use herein are nonionic surfactants according to the formula $R^1O(E)_e(P)_pH$ where $R^1$ is a hydrocarbon chain of from about 2 to about 24 carbon atoms, E is ethylene oxide, P is propylene oxide, and e and p which represent the average degree of, respectively ethoxylation and propoxylation, are of from about 0 to about 24 (with the sum of e+p being at least 1). Preferably, the hydrophobic moiety of the nonionic compound can be a primary or secondary, straight or branched alcohol having from about 8 to about 24 carbon atoms.

Suitable nonionic surfactants include the condensation products of ethylene oxide and/or propylene oxide with an alcohol having a straight or branched alkyl chain, having from about 6 to about 22 carbon atoms, wherein the degree of alkoxylation (ethoxylation and/or propoxylation) is from about 1 to about 15, preferably from about 5 to about 12. Such suitable nonionic surfactants are commercially available from Shell, for instance, under the trade name Neodol® or from BASF under the trade name Lutensol®.

The composition may also include an anionic surfactant. Suitable anionic surfactants can be any commonly known by those skilled in the art. Preferably, the anionic surfactant includes an alkyl sulphonate or a mixture thereof; an alkyl aryl sulphonate or a mixture thereof; and mixtures thereof. Particularly suitable linear alkyl sulphonate includes $C_8$ sulphonate like Witconate NAS 8® commercially available from Witco. Other anionic surfactants useful herein include a salt (including, for example, sodium, potassium, ammonium, and substituted ammonium salts such as mono-, di- and triethanolamine salts) of soap, an alkyl sulphate, an alkyl aryl sulphate, an alkyl alkoxylated sulphate, a $C_8$-$C_{24}$ olefinsulfonate, a sulphonated polycarboxylic acid prepared by sulphonation of the pyrolyzed product of alkaline earth metal citrates, e.g., as described in British patent specification No. 1,082,179; an alkyl ester sulfonate such as $C_{14\text{-}16}$ methyl ester sulfonate; an acyl glycerol sulfonate, an alkyl phosphate, an isethionate such as an acyl isethionate, a N-acyl taurate, an alkyl succinamate, an acyl sarcosinate, a sulfate of alkylpolysaccharide such as an sulfate of alkylpolyglucoside (the nonionic nonsulfated compounds being described below), an alkyl polyethoxy carboxylate such as those of the formula $R^2O(CH_2CH_2O)_kCH_2COO\text{-}M^+$ wherein $R^2$ is a $C_8$-$C_{22}$alkyl, k is an integer from about 0 to about 10, and M is a soluble salt-forming cation. A resin acid and a hydrogenated resin acid are also suitable, such as a rosin, a hydrogenated rosin, and a resin acid and a hydrogenated resin acid present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

The composition may also include zwitterionic surfactants, especially where the composition contains both basic and acidic groups which form an inner salt giving both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylate and sulfonate, although other groups like sulfate, phosphonate, and the like can be used. Some common examples of zwitterionic surfactants (i.e. betaine/sulphobetaine) are described in U.S. Pat. Nos. 2,082,275, 2,702,279 and 2,255,082. For example coconut dimethyl betaine is commercially available from Seppic under the trade name of Amonyl 265®. Lauryl betaine is commercially available from Albright & Wilson under the trade name Empigen BB/L®. A further example of betaine is lauryl-imino-dipropionate commercially available from Rhodia under the trade name Mirataine H2C-HA®. Particularly preferred zwitterionic surfactants for use in embodiments wherein the composition is a hard surface cleaning composition is the sulfobetaine surfactant as it delivers optimum soap scum cleaning benefits. Examples of particularly suitable sulfobetaine surfactant include tallow bis(hydroxyethyl) sulphobetaine and cocoamido propyl hydroxy sulphobetaine which are commercially available from Rhodia and Witco, under the trade name of Mirataine CBS® and Rewoteric AM CAS 15® respectively.

The composition may also include an amphoteric surfactant such as an amine oxide. Examples of amine oxides for use herein are for instance coconut dimethyl amine oxide and $C_{12}$-$C_{16}$ dimethyl amine oxide. Said amine oxides may be commercially available from Clariant, Stepan, and AKZO (under the trade name Aromox®). Other suitable amphoteric surfactants for the purpose of the invention are the phosphine or sulfoxide surfactants.

The composition may include a solvent. Solvents are generally used to ensure preferred product quality for dissolution, thickness and aesthetics and to ensure better processing. The composition of the present invention may further comprise a solvent or a mixture thereof, as an optional ingredient. Typically, in embodiments wherein the composition is a hard surface cleaning composition, the composition may comprise from about 0.1% to about 10%, preferably from about 0.5% to about 5%, and more preferably from about 1% to about 3% by weight of the total composition of a solvent or a mixture thereof.

Suitable solvents include $C_1$-$C_5$ alcohols according to the formula $R^{10}$—OH wherein $R^{10}$ is a saturated alkyl group of from about 1 to about 5 carbon atoms, preferably from about 2 to about 4. Suitable alcohols are ethanol, propanol, isopropanol or mixtures thereof. Other suitable alcohols are alkoxylated $C_{1-8}$ alcohols according to the formula $R^{11}$-$(A_q)$-OH wherein $R^{11}$ is a alkyl group of from about 1 to about 8 carbon atoms, preferably from about 3 to about 6, and wherein A is an alkoxy group, preferably propoxy and/or ethoxy, and q is an integer of from 1 to 5, preferably from 1 to 2. Suitable alcohols are butoxy propoxy propanol (n-BPP), butoxy propanol (n-BP), butoxyethanol, or mixtures thereof. Suitable alkoxylated aromatic alcohols to be used herein are those according to the formula $R^{12}$—$(B)_r$—OH wherein $R^{12}$ is an alkyl substituted or non-alkyl substituted aryl group of from about 1 to about 20 carbon atoms, preferably from about 2 to about 15, and more preferably from about 2 to about 10, wherein B is an alkoxy group, preferably a butoxy, propoxy and/or ethoxy, and r is an integer of from 1 to 5, preferably from 1 to 2. A suitable aromatic alcohol to be used herein is benzyl alcohol. Suitable alkoxylated aromatic alcohol is benzylethanol and or benzylpropanol. Other suitable solvent includes butyl diglycolether, benzylalcohol, propoxypropoxypropanol (EP 0 859 044) ether and diether, glycol, alkoxylated glycol, $C_6$-$C_{16}$ glycol ether, alkoxylated aromatic alcohol, aromatic alcohol, aliphatic branched alcohol, alkoxylated aliphatic branched alcohol, alkoxylated linear $C_1$-$C_5$ alcohol, linear $C_1$-$C_5$ alcohol, amine, $C_8$-$C_{14}$ alkyl and cycloalkyl hydrocarbon and halohydrocarbon, and mixtures thereof.

The composition of the present invention may comprise a perfume ingredient, or mixtures thereof, in amount up to about 5.0% by weight of the total composition, preferably in amount of about 0.1% to about 1.5%. Suitable perfume compounds and compositions for use herein are for example those described in EP-A-0 957 156 under the paragraph entitled "Perfume", on page 13.

The composition according to the present invention may be colored. Accordingly, it may comprise a dye or a mixture thereof. Suitable dyes for use herein are acid-stable dyes. By "acid-stable", it is meant herein a compound which is chemically and physically stable in the acidic environment of the composition herein.

The composition may include a pH adjustment agent such as an alkaline material or an acidic material. If an alkaline material is used, it may be present to trim the pH and/or maintain the pH of the composition according to the present invention. The amount of alkaline material is from about 0.001% to about 20%, preferably from about 0.01% to about 10%, and more preferably from about 0.05% to about 3% by weight of the composition. Examples of the alkaline material are sodium hydroxide, potassium hydroxide and/or lithium hydroxide, and/or the alkali metal oxide, such as sodium and/or potassium oxide, or mixtures thereof. Preferably, the source of alkalinity is sodium hydroxide or potassium hydroxide, preferably sodium hydroxide.

If the composition includes an acidic pH adjustment agent, it may include any suitable acid known to those skilled in the art. Typically the composition herein may comprise up to about 20%, preferably from about 0.1% to about 10%, more preferably from about 0.1% to about 5%, even more preferably from about 0.1% to about 3%, by weight of the total composition of an acid. Suitable acids are selected from the group consisting of a mono- and poly-carboxylic acid or a mixture thereof; a percarboxylic acid or a mixture thereof; a substituted carboxylic acid or a mixture thereof; and mixtures thereof. Carboxylic acids useful herein include $C_{1-6}$ linear or at least about 3 carbon containing cyclic acids. The linear or cyclic carbon-containing chain of the carboxylic acid may be substituted with a substituent group selected from the group consisting of hydroxyl, ester, ether, aliphatic groups having from about 1 to about 6, more preferably from about 1 to about 4 carbon atoms, and mixtures thereof. Suitable mono- and poly-carboxylic acids are selected from the group consisting of citric acid, lactic acid, ascorbic acid, isoascorbic acid, tartaric acid, formic acid, maleic acid, malic acid, malonic acid, propionic acid, acetic acid, dehydroacetic acid, benzoic acid, hydroxy benzoic acid, and mixtures thereof. Suitable percarboxylic acids are selected from the group consisting of peracetic acid, percarbonic acid, perboric acid, and mixtures thereof. Suitable substituted carboxylic acids are selected from the group consisting of an amino acid or a mixture thereof; a halogenated carboxylic acid or a mixture thereof; and mixtures thereof. Preferred acids for use herein are selected from the group consisting of lactic acid, citric acid, and ascorbic acid and mixtures thereof. More preferred acids for use herein are selected from the group consisting of lactic acid and citric acid and mixtures thereof. An even more preferred acid for use herein is lactic acid. Suitable acids are commercially available from JBL, T&L, or Sigma. Lactic acid is commercially available from Sigma and Purac.

The composition may also include a salt, for example, as a pH buffer. Salts are generally present at an active level of from about 0.01% to about 5%, from about 0.015% to about 3%, or from about 0.025% to about 2.0%, by weight of the composition. When salts are included, the ions can be selected from magnesium, sodium, potassium, calcium, and/or magnesium, and preferably from sodium and magnesium, and are added as a hydroxide, chloride, acetate, sulphate, formate, oxide or nitrate salt to the composition of the present invention.

In another preferred embodiment, the composition of the present invention comprises a diamine or a mixture thereof as the pH buffer. The composition will preferably contain from about 0% to about 15%, preferably from about 0.1% to about 15%, preferably from about 0.2% to about 10%, more preferably from about 0.25% to about 6%, more preferably from about 0.5% to about 1.5% by weight of the total composition of at least one diamine. Preferred organic diamines are those in which $pK_1$ and $pK_2$ are in the range of from about 8.0 to about 11.5, preferably in the range of from about 8.4 to about 11, even more preferably from about 8.6 to about 10.75. Preferred materials include 1,3-bis(methylamine) cyclohexane (pKa=from about 10 to about 10.5), 1,3-propane diamine (pK$_1$=10.5; pK$_2$=8.8), 1,6-hexane diamine (pK$_1$=11; pK$_2$=10), 1,3-pentane diamine (DYTEK EP®) (pK$_1$=10.5; pK$_2$=8.9), 2-methyl-1,5-pentane diamine (DYTEK A®) (pK$_1$=11.2; pK$_2$=10.0). Other preferred materials include primary/primary diamines with alkylene spacers ranging from C$_4$ to C$_8$. In general, it is believed that primary diamines are preferred over secondary and tertiary diamines. pKa is used herein in the same manner as is commonly known to people skilled in the art of chemistry: in an all-aqueous solution at 25° C. and for an ionic strength between about 0.1 to about 0.5 M. values. Reference can be obtained from literature, such as from "Critical Stability Constants: Volume 2, Amines" by Smith and Martel, Plenum Press, N Y and London, 1975.

The composition may also include a chelant. For example, the composition of the present invention may comprise a chelant at a level of from about 0.1% to about 20%, preferably from about 0.2% to about 5%, more preferably from about 0.2% to about 3% by weight of total composition. Suitable chelants can be selected from the group consisting of an amino carboxylate or a mixture thereof; an amino phosphonate or a mixture thereof; a polyfunctionally-substituted aromatic chelant or a mixture thereof; and mixtures thereof. Preferred chelants for use herein are the amino acid based chelants, and preferably glutamic-N,N-diacetic acid (GLDA) and derivatives, and/or phosphonate based chelants, and preferably diethylenetriamine pentamethylphosphonic acid. GLDA (salts and derivatives thereof) is especially preferred according to the invention, with the tetrasodium salt thereof being especially preferred. Also preferred are amino carboxylates including ethylenediaminetetra-acetate, N-hydroxyethylethylenediaminetriacetate, nitrilo-triacetate, ethylenediamine tetrapro-prionate, triethylenetetraaminehexacetate, diethylenetriaminepentaacetate, ethanoldi-glycine; and alkali metal, ammonium, and substituted ammonium salts thereof; and mixtures thereof; as well as MGDA (methyl-glycine-diacetic acid), and salts and derivatives thereof.

Other chelants include homopolymers and copolymers of polycarboxylic acids and their partially or completely neutralized salts, monomeric polycarboxylic acids and hydroxycarboxylic acids and their salts. Preferred salts of the above-mentioned compounds are the ammonium and/or alkali metal salts, i.e. the lithium, sodium, and potassium salts, and particularly preferred salts are the sodium salts. Suitable polycarboxylic acids are acyclic, alicyclic, heterocyclic and aromatic carboxylic acids, in which case they contain at least about two carboxyl groups which are in each case separated from one another by, preferably, no more than about two carbon atoms. Polycarboxylates which comprise two carboxyl groups include, for example, water-soluble salts of, malonic acid, (ethyl enedioxy) diacetic acid, maleic acid, diglycolic acid, tartaric acid, tartronic acid and fumaric acid. Polycarboxylates which contain three carboxyl groups include, for example, water-soluble citrate. Correspondingly, a suitable hydroxycarboxylic acid is, for example, citric acid. Another suitable polycarboxylic acid is the homopolymer of acrylic acid. Preferred are the polycarboxylates end capped with sulfonates. Further suitable polycarboxylates chelants for use herein include acetic acid, succinic acid, formic acid; all preferably in the form of a water-soluble salt. Other suitable polycarboxylates are oxodisuccinates, carboxymethyloxysuccinate and mixtures of tartrate monosuccinic and tartrate disuccinic acid such as described in U.S. Pat. No. 4,663,071.

Amino phosphonates are also suitable for use as chelant and include ethylenediaminetetrakis (methylenephosphonates) as DEQUEST. Preferably, these amino phosphonates do not contain alkyl or alkenyl groups with more than about 6 carbon atoms. Polyfunctionally-substituted aromatic chelants are also useful in the composition herein, such as described in U.S. Pat. No. 3,812,044. Preferred compounds of this type in acid form are dihydroxydisulfobenzenes such as 1,2-dihydroxy-3,5-disulfobenzene.

The composition of the present invention may optionally comprise a hydrotrope in an effective amount so that the composition is appropriately compatible in water. The composition of the present invention typically comprises from about 0% to about 15% by weight of the total composition of a hydrotropic, or mixtures thereof, preferably from about 1% to about 10%, preferably from about 3% to about 6%. Suitable hydrotropes for use herein include anionic-type hydrotropes, particularly sodium, potassium, and ammonium xylene sulphonate, sodium, potassium and ammonium toluene sulphonate, sodium potassium and ammonium cumene sulphonate, and mixtures thereof, and related compounds, as disclosed in U.S. Pat. No. 3,915,903.

The composition of the present invention may optionally contain a polymeric suds stabilizer. These polymeric suds stabilizers provide extended suds volume and suds duration of the composition. The composition preferably contains from about 0.01% to about 15%, preferably from about 0.05% to about 10%, more preferably from about 0.1% to about 5%, by weight of the total composition of the polymeric suds booster/stabilizer. These polymeric suds stabilizers may be selected from homopolymers of a (N,N-dialkylamino) alkyl ester and a (N,N-dialkylamino) alkyl acrylate ester. The weight average molecular weight of the polymeric suds booster, determined via conventional gel permeation chromatography, is from about 1,000 to about 2,000,000, preferably from about 5,000 to about 1,000,000, more preferably from about 10,000 to about 750,000, more preferably from about 20,000 to about 500,000, even more preferably from about 35,000 to about 200,000. The polymeric suds stabilizer can optionally be present in the form of a salt, either an inorganic or organic salt, for example the citrate, sulphate, or nitrate salt of (N,N-dimethylamino)alkyl acrylate ester.

One preferred polymeric suds stabilizer is (N,N-dimethylamino)alkyl acrylate ester, namely the acrylate ester represented by the formula (VII):

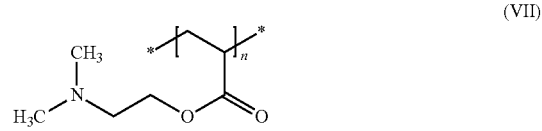

(VII)

Other preferred suds boosting polymers are copolymers of hydroxypropylacrylate/dimethyl aminoethylmethacrylate (copolymer of HPA/DMAM), represented by the formulae VIII and IX

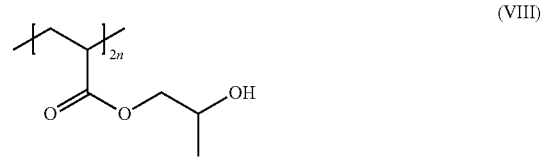

(VIII)

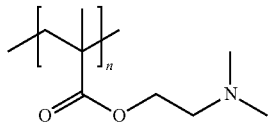

(IX)

Another preferred class of polymeric suds booster polymers are hydrophobically modified cellulosic polymers having a weight average molecular weight ($M_w$) below about 45,000; preferably between about 10,000 and about 40,000; more preferably between about 13,000 and about 25,000. The hydrophobically modified cellulosic polymers include water soluble cellulose ether derivatives, such as nonionic and cationic cellulose derivatives. Preferred cellulose derivatives include methylcellulose, hydroxypropyl methylcellulose, hydroxyethyl methylcellulose, and mixtures thereof.

The cleaning composition can comprise a thickener. An increased viscosity, especially low shear viscosity, provides longer contact time and therefore improved penetration of greasy soil and/or particulated greasy soil to improve cleaning effectiveness, especially when applied neat to the surface to be treated. Moreover, a high low shear viscosity improves the phase stability of the liquid cleaning composition, and especially improves the stability of the copolymer in compositions in the liquid hard surface cleaning composition. Suitable thickeners include polyacrylate based polymers, preferably hydrophobically modified polyacrylate polymers; hydroxyl ethyl cellulose, preferably hydrophobically modified hydroxyl ethyl cellulose, xanthan gum, hydrogenated castor oil (HCO) and mixtures thereof. Preferred thickeners are polyacrylate based polymers, preferably hydrophobically modified polyacrylate polymers. Preferably a water soluble copolymer based on main monomers acrylic acid, acrylic acid esters, vinyl acetate, methacrylic acid, acrylonitrile and mixtures thereof, more preferably copolymer is based on methacrylic acid and acrylic acid esters having appearance of milky, low viscous dispersion. One preferred hydrologically modified polyacrylate polymer is Rheovis® AT 120, which is commercially available from BASF.

When used, the cleaning composition may comprises from 0.1% to 10.0% by weight of the total composition of said thickener, preferably from 0.2% to 5.0%, more preferably from 0.2% to 2.5% and preferably from 0.2% to 2.0%.

The cleaning composition may comprise an additional polymer. It has been found that the presence of a specific polymer as described herein, when present, allows further improving the grease removal performance of the liquid composition due to the specific sudsing/foaming characteristics they provide to the composition. Suitable polymers for use herein are disclosed in co-pending EP patent application EP2272942 (09164872.5) and granted European patent EP2025743 (07113156.9). The polymer can be selected from the group consisting of: a vinylpyrrolidone homopolymer (PVP); a polyethyleneglycol dimethylether (DM-PEG); a vinylpyrrolidone/dialkylaminoalkyl acrylate or methacrylate copolymers; a polystyrenesulphonate polymer (PSS); a poly vinyl pyridine-N-oxide (PVNO); a polyvinylpyrrolidone/vinylimidazole copolymer (PVP-VI); a polyvinylpyrrolidone/polyacrylic acid copolymer (PVP-AA); a polyvinylpyrrolidone/vinylacetate copolymer (PVP-VA); a polyacrylic polymer or polyacrylicmaleic copolymer; and a polyacrylic or polyacrylic maleic phosphono end group copolymer; and mixtures thereof. Typically, the liquid hard surface cleaning composition may comprise from 0.005% to 5.0% by weight of the total composition of said polymer, preferably from 0.10% to 4.0%, more preferably from 0.1% to 3.0% and preferably from 0.20% to 1.0%.

The cleaning composition may comprise a fatty acid as a highly preferred optional ingredient, particularly as suds suppressors. Fatty acids are desired herein as they reduce the sudsing of the liquid composition when the composition is rinsed off the surface to which it has been applied. Suitable fatty acids include the alkali salts of a $C_8$-$C_{24}$ fatty acid. Such alkali salts include the metal fully saturated salts like sodium, potassium and/or lithium salts as well as the ammonium and/or alkylammonium salts of fatty acids, preferably the sodium salt. Preferred fatty acids for use herein contain from 8 to 22, preferably from 8 to 20 and more preferably from 8 to 18 carbon atoms. Suitable fatty acids may be selected from caprylic acid, capric acid, lauric acid, myristic acid, palmitic acid, stearic acid, oleic acid, and mixtures of fatty acids suitably hardened, derived from natural sources such as plant or animal esters (e.g., palm oil, olive oil, coconut oil, soybean oil, castor oil, tallow, ground oil, whale and fish oils and/or babassu oil. For example coconut fatty acid is commercially available from KLK OLEA under the name PALMERAB1211. Typically, the liquid hard surface cleaning composition may comprise up to 6.0% by weight of the total composition of said fatty acid, preferably from 0.1% to 3.0%, more preferably from 0.1% to 2.0% and preferably from 0.15% to 1.5% by weight of the total composition of said fatty acid.

The cleaning composition may comprise a branched fatty alcohol, particularly as suds suppressors. Suitable branched fatty alcohols include the 2-alkyl alkanols having an alkyl chain comprising from 6 to 16, preferably from 7 to 13, more preferably from 8 to 12, preferably from 8 to 10 carbon atoms and a terminal hydroxy group, said alkyl chain being substituted in the α position (i.e., position number 2) by an alkyl chain comprising from 1 to 10, preferably from 2 to 8 and more preferably 4 to 6 carbon atoms. Such suitable compounds are commercially available, for instance, as the Isofol® series such as Isofol® 12 (2-butyl octanol) or Isofol® 16 (2-hexyl decanol) commercially available from Sasol. Typically, the liquid hard surface cleaning composition may comprise up to 2.0% by weight of the total composition of said branched fatty alcohol, preferably from 0.10% to 1.0%, more preferably from 0.1% to 0.8% and preferably from 0.1% to 0.5%.

The cleaning compositions described herein may include from about 0.1% to about 10%, in some examples, from about 0.2% to about 5%, and in other examples, from about 0.5% to about 3%, by weight the composition, of a polyetheramine.

In some aspects, the polyetheramine is represented by the structure of Formula (I):

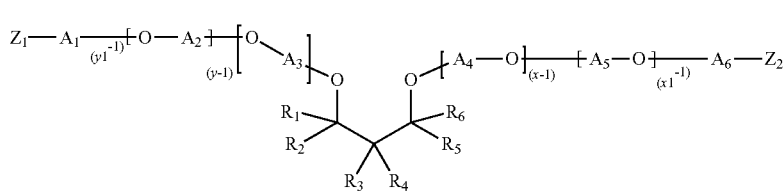

Formula (I)

where each of $R_1$-$R_6$ is independently selected from H, alkyl, cycloalkyl, aryl, alkylaryl, or arylalkyl, where at least one of $R_1$-$R_6$ is different from H, typically at least one of $R_1$-$R_6$ is an alkyl group having 2 to 8 carbon atoms, each of $A_1$-$A_6$ is independently selected from linear or branched alkylenes having 2 to 18 carbon atoms, typically 2 to 10 carbon atoms, more typically, 2 to 5 carbon atoms, each of $Z_1$-$Z_2$ is independently selected from OH or $NH_2$, where at least one of $Z_1$-$Z_2$ is $NH_2$, typically each of $Z_1$ and $Z_2$ is $NH_2$, where the sum of x+y is in the range of about 2 to about 200, typically about 2 to about 20 or about 3 to about 20, more typically about 2 to about 10 or about 3 to about 8 or about 4 to about 6, where x≥1 and y≥1, and the sum of $x_1$+$y_1$ is in the range of about 2 to about 200, typically about 2 to about 20 or about 3 to about 20, more typically about 2 to about 10 or about 3 to about 8 or about 2 to about 4, where $x_1$≥1 and $y_1$≥1.

In some aspects, the polyetheramine is represented by the structure of Formula (II):

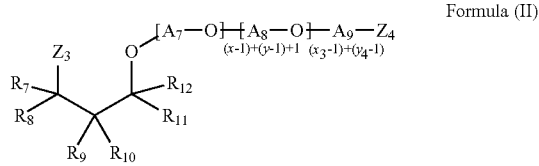

Formula (II)

where each of $R_7$-$R_{12}$ is independently selected from H, alkyl, cycloalkyl, aryl, alkylaryl, or arylalkyl, where at least one of $R_7$-$R_{12}$ is different from H, typically at least one of $R_7$-$R_{12}$ is an alkyl group having 2 to 8 carbon atoms, each of $A_7$-$A_9$ is independently selected from linear or branched alkylenes having 2 to 18 carbon atoms, typically 2 to 10 carbon atoms, more typically, 2 to 5 carbon atoms, each of $Z_3$-$Z_4$ is independently selected from OH or $NH_2$, where at least one of $Z_3$-$Z_4$ is $NH_2$, typically each of $Z_3$ and $Z_4$ is $NH_2$, where the sum of x+y is in the range of about 2 to about 200, typically about 2 to about 20 or about 3 to about 20, more typically about 2 to about 10 or about 3 to about 8 or about 2 to about 4, where x≥1 and y≥1, and the sum of $x_1$+$y_1$ is in the range of about 2 to about 200, typically about 2 to about 20 or about 3 to about 20, more typically about 2 to about 10 or about 3 to about 8 or about 2 to about 4, where $x_1$≥1 and $y_1$≥1.

The liquid hard surface cleaning compositions may comprise a variety of other optional ingredients depending on the technical benefit aimed for and the surface treated. Suitable optional ingredients for use herein include perfume, builders, other polymers, buffers, bactericides, hydrotropes, colorants, stabilisers, radical scavengers, abrasives, soil suspenders, brighteners, anti-dusting agents, dispersants, dye transfer inhibitors, pigments, silicones and/or dyes.

The composition may also include a cleaning composition comprising at least one fluorinated carbon compound (e.g. perfluoropolyether) and at least one of the following components: a) a non-fluorinated solvent; and b) a surfactant. Examples of such compositions are disclosed in EP 1440140.

One example of a hard surface cleaning composition is set forth in the following table:

TABLE 1

|  | Wt % |
|---|---|
| Ethoxylated alkoxylated nonionic surfactant | 0.001-0.05% |
| Additional Nonionic Surfactant | 0.01-0.5% |
| Glycol ether based solvent | 0.1-0.5% |
| Quaternary Compound | 0.01-0.08% |
| Suds Suppressor | 0.001-0.5% |
| Minors and Water | to 100% |
| pH | 6-8 |

Sanitizing Compsitions:

The method and device of the present invention may also be used to sanitize discrete areas of a surface. Similar to cleaning, this can help reduce the amount of active material to be used and can target very specific areas in order to not damage the surrounding surface or environment.

The composition may include any sanitizing composition known to those of ordinary skill in the relevant art, including, but not limited to, alkyl halohydantoins, alkali metal haloisocyanurates, bleach, essential oils, non-quaternary ammonium based germicidal compounds as well as quaternary ammonium germicidal compounds. Other sanitizing compositions include quaternary ammonium compounds and salts thereof, including C8-C18 amine oxides and C12-C22 alk(en)yl morpholinium salts, C8-C12 protonated amine compounds, including N,N-bis(3-aminopropyl)lauramine, as well as C8-C12 dialkyl dimethyl ammonium salts and C12-C18 alkyl dimethyl benzyl ammonium salts, and mixtures thereof. The composition may also include hydrogen peroxide and oxygen-release bleaching agents, such as, for example, alkali metal perborates, e.g., sodium perborate, and alkali metal monopersulfates, e.g., sodium monopersulfates, potassium monopersulfate, alkali metal monoperphosphates, e.g., disodium monoperphosphate and dipotassium monoperphosphate, as well as other conventional bleaching agents capable of liberating hypohalite, e.g., hypochlorite and/or hypobromite, include heterocyclic N-bromo- and N-chloro-cyanurates such as trichloroisocyanuric and tribromoiscyanuric acid, dibromocyanuric acid, dichlorocyanuric acid, N-monobromo-N-mono-chlorocyanuric acid and N-monobromo-N,N-dichlorocyanuric acid, as well as the salts thereof with water solubilizing cations such as potassium and sodium, e.g., sodium N-monobromo-N-monochlorocyanurate, potassium dichlorocyanurate, sodium dichlorocyanurate, as well as other N-bromo and N-chloro-imides, such as N-brominated and N-chlorinated succinimide, malonimide, phthalimide and naphthalimide.

The composition may also include solid peracids such as phtalimidoperhexanoic acid (PAP), nonoylbenzene sulfonate, m-chloro perbenzoic acid, as well as C1-C12 peroxyacids which are formed as equilibrium mixtures in acidic media in the presence of hydrogen peroxide. Preferred peraoxyacids are peroxyacetic acid, peroxyoctanoic acid and peroxynonanoic acid, and mixtures thereof.

The composition may also include biguanides which are hydrophilic cationic molecules, and the compounds of potential interest include chlorhexidine slats (diacetate, digluconate, etc.) and polyhexamethylene biguanide (PHMB) comprising from about 5 to about 25 repeat units on average.

The composition may also include iodine, iodine salts such potassium iodate (KIO3), and iodophors including iodine complexes formed with nonionic surfactants and complexes with polyvinyl pyrrolidone (PVP-I2), and mixtures thereof.

The composition may also include organic acids, such as, for example, citric acid, lactic acid, acetic acid, glycolic acid, succinic acid, malonic acid, maleic acid, octanoic acid and 2-hydroxypropionic acid, and mixtures thereof. Especially preferred are citric acid and lactic acid.

The composition may also include antimicrobial metal salts. This class generally includes salts of metals in groups 3b-7b, 8 and 3a-5a. Specifically are the salts of aluminum, zirconium, zinc, silver, gold, copper, lanthanum, tin, bismuth, selenium, strontium, scandium, yttrium, cerium, praseodymiun, neodymium, promethum, samarium, europium, gadolinium, terbium, dysprosium, holmium, erbium, thulium, ytterbium, lutetium and mixtures thereof.

The composition may also include germicidally effective agents useful as sanitizing agents include sodium dichloroisocyanurate (DCCNa) and sodium dibromoisocyanurate. Examples of non-quaternary ammonium based sanitizing agents include pyrithiones, dimethyldimethylol hydantoin, methylchloroisothiazolinone/methylisothiazolinone sodium sulfite, sodium bisulfate, imidazolidinyl urea, diazolidinyl urea, benzyl alcohol, 2-bromo-2-nitropropane-1,3-diol, formalin (formaldehyde), iodopropenyl butylcarbamate, chloroacetamide, methanamine, methyl dibromonitrile glutaronitrile, glutaraldehyde, 5-bromo-5-nitro-1,3-dioxane, phenethyl alcohol, o-phenylphenol/sodium o-phenylphenol, sodium hydroxymethylglycinate, polymethoxy bicyclic oxazolidine, dimethoxane, thimersal dichlorobenzyl alcohol, captan, chlorphenenesin, dichlorophene, chlorbutanol, glyceryl laurate, halogenated diphenyl ethers, phenolic compounds, mono- and poly-alkyl and aromatic halophenols, resorcinol and its derivatives, bisphenolic compounds, benzoic esters (parabens), halogenated carbanilides, 3-trifluoromethyl-4,4'-dichlorocarbanilide, and 3,3',4-trichlorocarbanilide. More preferably, the non-cationic antimicrobial agent is a mono- and poly-alkyl and aromatic halophenol selected from the group p-chlorophenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m, m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl p-chlorophenol, 6-diethylmethyl-3-methyl p-chlorophenol, 6-iso-propyl-2-ethyl-3-methyl p-chlorophenol, 2-sec-amyl-3,5-dimethyl p-chlorophenol 2-diethylmethyl-3,5-dimethyl p-chlorophenol, 6-sec-octyl-3-methyl p-chlorophenol, p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol, dichloro meta xylenol, chlorothymol, and 5-chloro-2-hydroxydiphenylmethane.

Suitable exemplary sanitizing compositions are described in more detail in U.S. Pat. Nos. 5,122,541, 6,346,279; 7,632,523.

Spot Cleaning:

The method and device of the present invention may also be used for surface spot cleaning and/or deodorizing of surfaces and materials such as carpeting, drapes, blinds, clothing, wall-paper, and the like. Examples of suitable compositions for use with the device and method of the present invention are disclosed in WO 95/04127; WO 96/015308; and WO 200026329.

The composition may also include one or more enzymes. Suitable enzymes include proteases, amylases, cellulases, lipases, xylogucanases, pectate lyases, mannanases, bleaching enzymes, cutinases, and mixtures thereof.

For the enzymes, accession numbers or IDs shown in parentheses refer to the entry numbers in the databases Genbank, EMBL and Swiss-Prot. For any mutations standard 1-letter amino acid codes are used with a * representing a deletion. Accession numbers prefixed with DSM refer to microorgansims deposited at Deutsche Sammlung von Mikroorganismen und Zellkulturen GmbH, Mascheroder Weg 1b, 38124 Brunswick (DSMZ).

The composition may comprise a protease. Suitable proteases include metalloproteases and/or serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, Bacillus alkalophilus* (P27963, ELYA_BACAO), *Bacillus subtilis, Bacillus amyloliquefaciens* (P00782, SUBT_BACAM), *Bacillus pumilus* (P07518) and *Bacillus gibsonii* (DSM14391).

(b) trypsin-type or chymotrypsin-type proteases, such as trypsin (e.g. of porcine or bovine origin), including the *Fusarium* protease and the chymotrypsin proteases derived from Cellumonas (A2RQE2).

(c) metalloproteases, including those derived from *Bacillus amyloliquefaciens* (P06832, NPRE_BACAM).

Preferred proteases include those derived from *Bacillus gibsonii* or *Bacillus Lentus* such as subtilisin 309 (P29600) and/or DSM 5483 (P29599).

Suitable commercially available protease enzymes include: those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase® and Purafect OXP® by Genencor International; those sold under the tradename Opticlean® and Optimase® by Solvay Enzymes; those available from Henkel/Kemira, namely BLAP (P29599 having the following mutations S99D+S101 R+S103A+V104I+G159S), and variants thereof including BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D) all from Henkel/Kemira; and KAP (*Bacillus alkalophilus* subtilisin with mutations A230V+S256G+S259N) from Kao.

Suitable amylases are alpha-amylases, including those of bacterial or fungal origin. Chemically or genetically modified mutants (variants) are included. A preferred alkaline alpha-amylase is derived from a strain of *Bacillus*, such as *Bacillus licheniformis*, *Bacillus amyloliquefaciens*, *Bacillus stearothermophilus*, *Bacillus subtilis*, or other *Bacillus* sp., such as *Bacillus* sp. NCIB 12289, NCIB 12512, NCIB 12513, sp 707, DSM 9375, DSM 12368, DSMZ no. 12649, KSM AP1378, KSM K36 or KSM K38. Preferred amylases include: (a) alpha-amylase derived from *Bacillus licheniformis* (P06278, AMY_BACLI), and variants thereof, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444 (b) AA560 amylase (CBU30457, HD066534) and variants thereof, especially the variants with one or more substitutions in the following positions: 26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184* (c) variants exhibiting at least 90% identity with the wild-type enzyme from *Bacillus* SP722 (CBU30453, HD066526), especially variants with deletions in the 183 and 184 positions.

Suitable commercially available alpha-amylases are Duramyl®, Liquezyme® Termamyl®, Termamyl Ultra®, Natalase®, Supramyl®, Stainzyme®, Stainzyme Plus®, Fungamyl® and BAN® (Novozymes A/S), Bioamylase® and variants thereof (Biocon India Ltd.), Kemzym® AT 9000 (Biozym Ges. m.b.H, Austria), Rapidase®, Purastar®, Optisize HT Plus®, Enzysize®, Powerase® and Purastar Oxam®, Maxamyl® (Genencor International Inc.) and KAM® (KAO, Japan). Preferred amylases are Natalase®, Stainzyme® and Stainzyme Plus®.

The composition may comprise a cellulase. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum*.

Commercially available cellulases include Celluzyme®, and Carezyme® (Novozymes A/S), Clazinase®, and Puradax HA® (Genencor International Inc.), and KAC-500 (B)® (Kao Corporation).

In one aspect, the cellulase can include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403) and mixtures thereof. Suitable endoglucanases are sold under the tradenames Celluclean® and Whitezyme® (Novozymes A/S, Bagsvaerd, Denmark).

Preferably, the composition comprises a cleaning cellulase belonging to Glycosyl Hydrolase family 45 having a molecular weight of from 17 kDa to 30 kDa, for example the endoglucanases sold under the tradename Biotouch® NCD, DCC and DCL (AB Enzymes, Darmstadt, Germany).

Highly preferred cellulases also exhibit xyloglucanase activity, such as Whitezyme®.

The composition may comprise a lipase. Suitable lipases include those of bacterial or fungal origin. Chemically modified or protein engineered mutants are included. Examples of useful lipases include lipases from *Humicola* (synonym *Thermomyces*), e.g., from *H. lanuginosa* (T *lanuginosus*), or from *H. insolens*, a *Pseudomonas* lipase, e.g., from *P. alcaligenes* or *P. pseudoalcaligenes, P. cepacia, P. stutzeri, P. fluorescens, Pseudomonas* sp. strain SD 705, *P. wisconsinensis*, a *Bacillus* lipase, e.g., from *B. subtilis, B. stearothermophilus* or *B. pumilus*.

The lipase may be a "first cycle lipase", preferably a variant of the wild-type lipase from *Thermomyces lanuginosus* comprising T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Preferred lipases would include those sold under the tradenames Lipex®, Lipolex® and Lipoclean® by Novozymes, Bagsvaerd, Denmark.

Preferably, the composition comprises a variant of *Thermomyces lanuginosa* (O59952) lipase having >90% identity with the wild type amino acid and comprising substitution(s) at T231 and/or N233, preferably T231R and/or N233R.

In another aspect, the composition comprises a variant of *Thermomyces lanuginosa* (O59952) lipase having >90% identity with the wild type amino acid and comprising substitution(s):

(a) S58A+V60S+I83T+A150G+L227G+T231R+N233R+I255A+P256K;

(b) S58A+V60S+I86V+A150G+L227G+T231R+N233R+I255A+P256K;

(c) S58A+V60S+I86V+T143S+A150G+L227G+T231R+N233R+I255A+P256K;

(d) S58A+V60S+I86V+T143S+A150G+G163K+S216P+L227G+T231R+N233R+I255A+P256K;

(e) E1*+S58A+V60S+I86V+T143S+A150G+L227G+T231R+N233R+I255A+P256K;

(f) S58A+V60S+I86V+K98I+E99K+T143S+A150G+L227G+T231R+N233R+I255A+P256K;

(g) E1N+S58A+V60S+I86V+I(98I+E99K+T143S+A150G+L227G+T231R+N233R+I255A+P256K+L259F;

(h) S58A+V60S+I86V+K98I+E99K+D102A+T143S+A150G+L227G+T231R+N233R+I255A+P256K;

(i) N33Q+S58A+V60S+I86V+T143S+A150G+L227G+T231R+N233R+I255A+P256K;

(j) E1*+S58A+V60S+I86V+K98I+E99K+T143S+A150G+L227G+T231R+N233R+I255A+P256K;

(k) E1N+S58A+V60S+I86V+I(98I+E99K+T143S+A150G+S216P+L227G+T231R+N233R+I255A+P256K;

(l) D27N+S58A+V60S+I86V+G91N+N94R+D1 U N+T143S+A150G+L227G+T231R+N233R+I255A+P256K;

(m) E1N+S58A+V60S+I86V+I(98I+E99K+T143S+A150G+E210A+S216P+L227G+T231R+N233R+I255A+P256K;

(n) A150G+E210V+T231R+N233R+I255A+P256K; and (o) I202L+E210G+T231R+N233R+I255A+P256K.

Suitable xyloglucanase enzymes have enzymatic activity towards both xyloglucan and amorphous cellulose substrates, wherein the enzyme is a glycosyl hydrolase (GH) is selected from GH families 5, 12, 44 or 74. Preferably, the glycosyl hydrolase is selected from GH family 44. Suitable glycosyl hydrolases from GH family 44 are the XYG1006 glycosyl hydrolase from *Paenibacillus polyxyma* (ATCC 832) and variants thereof.

Suitable pectate lyases are either wild-types or variants of *Bacillus*-derived pectate lyases (CAF05441, AAU25568) sold under the tradenames Pectawash®, Pectaway® and X-Pect® (from Novozymes A/S, Bagsvaerd, Denmark).

Suitable mannanases are sold under the tradenames Mannaway® (from Novozymes A/S, Bagsvaerd, Denmark), and Purabrite® (Genencor International Inc., Palo Alto, Calif.).

Suitable bleach enzymes include oxidoreductases, for example oxidases such as glucose, choline or carbohydrate oxidases, oxygenases, catalases, peroxidases, like halo-, chloro-, bromo-, lignin-, glucose- or manganese-peroxidases, dioxygenases or laccases (phenoloxidases, polyphenoloxidases). Suitable commercial products are sold under the Guardzyme® and Denilite® ranges from Novozymes. Advantageously, additional, preferably organic, particularly preferably aromatic compounds are incorporated with the bleaching enzyme; these compounds interact with the bleaching enzyme to enhance the activity of the oxidoreductase (enhancer) or to facilitate the electron flow (mediator) between the oxidizing enzyme and the stain typically over strongly different redox potentials.

Other suitable bleaching enzymes include perhydrolases, which catalyse the formation of peracids from an ester substrate and peroxygen source. Suitable perhydrolases include variants of the *Mycobacterium smegmatis* perhydrolase, variants of so-called CE-7 perhydrolases, and variants of wild-type subtilisin Carlsberg possessing perhydrolase activity.

Suitable cutinases are defined by E.C. Class 3.1.1.73, preferably displaying at least 90%, or 95%, or most preferably at least 98% identity with a wild-type derived from one of *Fusarium solani, Pseudomonas Mendocina* or *Humicola Insolens*.

The relativity between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

Alkoxylated polycarboxylates such as those prepared from polyacrylates are useful herein to provide additional grease removal performance. Such materials are described in WO 91/08281 and PCT 90/01815. Chemically, these materials comprise polyacrylates having one ethoxy side-chain per every 7-8 acrylate units. The side-chains are of the formula —(CH2CH2O)m (CH2)nCH3 wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

The compositions disclosed herein may also comprise amphiphilic graft co-polymers. In some aspects, the amphiphilic graft co-polymer comprises (i) a polyethyelene glycol backbone; and (ii) and at least one pendant moiety selected from polyvinyl acetate, polyvinyl alcohol and mixtures thereof. A preferred amphiphilic graft co-polymer is Sokalan HP22, supplied from BASF.

Stain Prevention:

The method and device of the present invention may also be used for stain prevention on surfaces and materials. Stain prevention compositions that could be used with the present invention are described in more detailed in U.S. Pat. Nos. 8,633,146; and 8,637,442.

Pre-Treating:

The method and device of the present invention may also be used for pre-treating surfaces and materials. Pre-treating can help make cleaning and other tasks easier or can be used to place material onto a surface in anticipation of a subsequent treatment or use of the surface or material. Pre-treating compositions that could be used with the present invention include, but are not limited to simple short chain alcohols, alcohol Alkoxylates and solvactants, such as C8P2, C6P1, etc. Additional pre-treating compositions include alkyl phenols and alkyl phenol ethoxylates such as, for example, C4-C6PhOH, C4-C6PhE1, etc. Yet other pre-treating compositions include longer chain alcohols and ethoxylates and glycerol ethers, such as, for example, C12, and C14.

Perfume and Malodor Control:

The method and device of the present invention may be used to dispense compositions including perfumes and malodor control substances. Often perfumes mask scents whereas malodor control technologies do not unduly interfere with the scent of the perfumed or unperfumed situs that is treated with the malodor control technology.

Suitable presumes may include materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, α-damascone, β-damascone, δ-damascone, β-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and β-dihydro ionone, linalool, ethyllinalool, tetrahydrolinalool, and dihydromyrcenol.

The compositions may comprise one or more perfume delivery technologies that stabilize and enhance the deposition and release of perfume ingredients from treated substrate. Such perfume delivery technologies can also be used to increase the longevity of perfume release from the treated substrate. Perfume delivery technologies, methods of making certain perfume delivery technologies and the uses of such perfume delivery technologies are disclosed in US 2007/0275866 A1.

In one aspect, the compositions of the present invention may comprise from about 0.001% to about 20%, or from about 0.01% to about 10%, or from about 0.05% to about 5%, or even from about 0.1% to about 0.5% by weight of the perfume delivery technology. In one aspect, said perfume delivery technologies may be selected from the group consisting of: perfume microcapsules, pro-perfumes, polymer particles, functionalized silicones, polymer assisted delivery, molecule assisted delivery, fiber assisted delivery, amine assisted delivery, cyclodextrins, starch encapsulated accord, zeolite and inorganic carrier, and mixtures thereof.

In one aspect, said perfume delivery technology may comprise microcapsules formed by at least partially surrounding a benefit agent with a wall material. Said benefit agent may include materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, α-damascone, β-damascone, δ-damascone, β-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and β-dihydro ionone, linalool, ethyllinalool, tetrahydrolinalool, and dihydromyrcenol. Suitable perfume materials can be obtained from Givaudan Corp. of Mount Olive, N.J., USA, International Flavors & Fragrances Corp. of South Brunswick, N.J., USA, or Quest Corp. of Naarden, Netherlands. In one aspect, the microcapsule wall material may comprise: melamine, polyacrylamide, silicones, silica, polystyrene, polyurea, polyurethanes, polyacrylate based materials, gelatin, styrene malic anhydride, polyamides, and mixtures thereof. In one aspect, said melamine wall material may comprise melamine cross-linked with formaldehyde, melamine-dimethoxyethanol crosslinked with formaldehyde, and mixtures thereof. In one aspect, said polystyrene wall material may comprise polyestyrene cross-linked with divinylbenzene. In one aspect, said polyurea wall material may comprise urea crosslinked with formaldehyde, urea crosslinked with gluteraldehyde, and mixtures thereof. In one aspect, said polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof. In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. In one aspect, the microcapsule may be a perfume microcapsule. In one aspect, one or more types of microcapsules, for example two microcapsules types having different benefit agents may be used.

In one aspect, the perfume delivery technology may comprise an amine reaction product (ARP) or a thio reaction product. One may also use "reactive" polymeric amines and or polymeric thiols in which the amine and/or thiol functionality is pre-reacted with one or more PRMs to form a reaction product. Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen and/or sulfur, for example oxygen, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

Examples of compostions that can be used for odor control include, but are not limited to, SPMB, FFEs, Cyclodextrin, malodor moderators, anti-Oxidants, Cremophor, BEEPA-like oligomers, cyclodextrin (disclosed in WO 200116266) and odor masking technologies such as Haloscent available from Firminich.

The following are examples of liquid compositions that can be used as odor control or freshening compositions.

Example 1

| | wt % Active | | | | |
|---|---|---|---|---|---|
| Ingredient | A | B | C | D | E |
| Deionized Water | Balance | Balance | Balance | Balance | Balance |
| Ethanol | 3.0 | 3.0 | 3.0 | 3.0 | 3.0 |
| Lupasol HF[1] | NIL | NIL | NIL | NIL | NIL |
| Hydroxypropyl b-CD | NIL | NIL | NIL | NIL | NIL |
| Diethylene Glycol | NIL | NIL | NIL | NIL | NIL |
| Silwet L-7600 | 0.1 | 0.1 | 0.1 | 0.100 | 0.100 |
| Basophor EL60[2] | NIL | 0.05 | 0.05 | 0.05 | 0.05 |
| Maleic Acid and/or Citric Acid[3] | As needed | As needed | As needed | As needed | As needed |
| Koralone B-119 | 0.015 | 0.015 | 0.015 | 0.015 | 0.015 |
| Hydroxypropyl β-cyclodextrin | NIL | NIL | NIL | NIL | NIL |
| Sodium Hydroxide[3] | As needed | As needed | As needed | As needed | As needed |
| Malodor Reducing Composition from EXAMPLE 2B | NIL | 0.05% | NIL | NIL | NIL |
| Malodor Reducing Composition from EXAMPLE 2C | NIL | NIL | 0.05% | NIL | NIL |
| Malodor Reducing Composition from EXAMPLE 3 | NIL | NIL | NIL | 0.05% | NIL |
| Malodor Reducing Composition from EXAMPLE 4 | NIL | NIL | NIL | NIL | 0.05% |
| Fragrance | 0 | 0 | 0 | 0 | 0 |
| Target pH | 6.8 | 6.8 | 6.8 | 6.8 | 6.8 |
| Total | 100 | 100 | 100 | 100 | 100 |

Example 2

| Ingredients | CAS# | % wt Active B | % wt Active C |
|---|---|---|---|
| 2,2,7,7-tetramethyltricyclo (6.2.1.0(1,6))-undecan-5-one | 23787-90-8 | 20 | 20 |
| 3-(3,3-dimethyl-2,3-dihydro-1H-inden-5-yl)propanal | 173445-65-3 | 7.5 | 10 |
| (E)-3,7-dimethylocta-2,6-dien-1-yl palmitate | 3681-73-0 | 40 | NIL |
| 3-methyl-5-phenylpentan-1-ol | 55066-48-3 | 10 | 10 |
| 3a,4,5,6,7,7a-hexahydro-4,7-methano-1H-inden-(5 and 6)-yl acetate | 5413-60-5 | 4 | 20 |
| 3-(6,6-dimethylbicyclo[3.1.1]hept-2-en-2-yl)-2,2-dimethylpropanal | 33885-52-8 | 10.000 | NIL |
| 3,4,4a,5,6,7,8,8a-octahydrochromen-2-one | 4430-31-3 | 5.000 | NIL |
| (E)-3,7-dimethylocta-1,3,6-triene | 3338-55-4 | 3.000 | NIL |
| 1-((2-(tert-butyl)cyclohexyl)oxy)butan-2-ol | 139504-68-0 | 0.500 | NIL |
| 2,2,7,7-tetramethyltricyclo(6.2.1.0(1,6))-undecan-5-one | 23787-90-8 | NIL | 20.000 |
| 7-methyloctyl acetate | 58430-94-7 | NIL | 40.000 |
| 1-((2-(tert-butyl)cyclohexyl)oxy)butan-2-ol | 139504-68-0 | to 100 | to 100 |

Example 3

| Ingredients | CAS# | % wt Active |
|---|---|---|
| 5-Cyclohexadecen-1-One | 37609-25-9 | 2.6 |
| 2,2,7,7,8,9,9-heptamethyldecahydroindeno[4,3a-b]furan | 647828-16-8 | 0.005 |
| 1,1,2,3,3-pentamethyl-1,2,3,5,6,7-hexahydro-4H-inden-4-one | 33704-61-9 | 0.3 |
| (3R,3aR,6S,7S,8aS)-6-methoxy-3,6,8,8-tetramethyloctahydro-1H-3a,7-methanoazulene | 19870-74-7 | 6 |
| Dodecanenitrile | 2437-25-4 | 0.06 |
| Trans 4-Decenal | 65405-70-1 | 0.001 |
| Decanal | 112-31-2 | 3 |
| (E)-3-methylcyclopentadec-4-en-1-one | 82356-51-2 | 0.4 |
| Oxydibenzene | 101-84-8 | 0.5 |
| Dipropylene Glycol | 25265-71-8 | 0.054 |
| 3a,4,5,6,7,7a-hexahydro-4,7-methano-1H-inden-(5 and 6)-yl acetate | 54830-99-8 | 4 |
| 3-(2-ethylphenyl)-2,2-dimethylpropanal | 67634-15-5 | 3 |
| 3-(3-isopropylphenyl)butanal | 125109-85-5 | 0.6 |
| 8,8-dimethyl-3a,4,5,6,7,7a-hexahydro-1H-4,7-methanoinden-6-yl propionate | 68912-13-0 | 6 |
| 2-(8-isopropyl-6-methylbicyclo[2.2.2]oct-5-en-2-yl)-1,3-dioxolane | 68901-32-6 | 10 |
| d E)-3,7-dimethylocta-2,6-dien-1-yl palmitate | 3681-73-0 | 10 |
| 7-methyloctyl acetate | 40379-24-6 | 3 |
| 2,2,7,7-tetramethyltricyclo(6.2.1.0(1,6))-undecan-5-one | 23787-90-8 | 10 |
| (1-methyl-2-((1,2,2-trimethylbicyclo[3.1.0]hexan-3-yl)methyl)cyclopropyl)methanol | 198404-98-7 | 0.1 |
| Dodecanal | 112-54-9 | 0.6 |
| Linalyl Benzoate | 126-64-7 | 1.74 |
| 4-(tert-butyl)cyclohexyl acetate | 32210-23-4 | 4 |
| octahydro-1H-4,7-methanoindene-1-carbaldehyde | 30772-79-3 | 0.26 |
| methyl 2-(3-oxo-2-pentylcyclopentyl)acetate | 24851-98-7 | 4.15 |
| (Z)-1,2-dimethoxy-4-(prop-1-en-1-yl)benzene | 93-16-3 | 18.23 |
| Methyl Palmitate | 112-39-0 | 3 |
| 3-(3,3-dimethyl-2,3-dihydro-1H-inden-5-yl)propanal | 300371-33-9 | 0.4 |
| 4-tert-butyl cyclohexanol | 98-52-2 | 0.05 |
| 3-methyl-5-phenylpentan-1-ol | 55066-48-3 | 3.5 |
| 2-isobutyl-4-methyltetrahydro-2H-pyran-4-ol | 63500-71-0 | 1.6 |
| (E)-4-methyldec-3-en-5-ol | 81782-77-6 | 0.8 |
| Undecanal | 112-44-7 | 1.7 |
| undec-10-enal | 112-45-8 | 0.35 |

Example 4

| Ingredients | CAS# | % wt Active |
|---|---|---|
| (3R,3aR,6S,7S,8aS)-6-methoxy-3,6,8,8-tetramethyloctahydro-1H-3a,7-methanoazulene | 19870-74-7 | 2.00 |
| 1-(1,2,3,4,5,6,7,8-octahydro-2,3,8,8-tetramethyl-2-naphthyl)ethan-l-one. | 54464-57-2 | 15.00 |
| Oxacyclohexadec-12-en-2-one, (12E)- | 1118-80-2 | 15.00 |
| 5-cyclohexadecenone | 37609-25-9 | 16.50 |
| 4,8-dimethyl-2-(propan-2-ylidene)-1,2,3,3a,4,5,6,8a-octahydroazulen-6-yl acetate | 117-98-6 | 5.00 |
| isopropyl tetradecanoate | 110-27-0 | 12.25 |
| (Z)-4,11,11-trimethyl-8-methylenebicyclo[7.2.0]undec-3-en-5-yl acetate | 32214-91-8 | 3.50 |
| (E)-cycloheptadec-9-en-1-one | 542-46-1 | 14.00 |
| (E)-cyclohexadec-8-en-1-one | 3100-36-5 | 14.00 |
| 4-((2R)-1,7,7-trimethylbicyclo[2.2.1]heptan-2-yl)cyclohexan-1-ol | 66072-32-0 | 2.75 |

Bleaching:

The composition may comprise bleach and/or bleaching agents. Suitable bleach includes bleach activators, sources of available oxygen, pre-formed peracids, bleach catalysts, reducing bleach, and any combination thereof. If present, the bleach, or any component thereof, for example the pre-formed peracid, may be coated, such as encapsulated, or clathrated, such as with urea or cyclodextrin.

Suitable bleach activators include: tetraacetylethylenediamine (TAED); oxybenzene sulphonates such as nonanoyl oxybenzene sulphonate (NOBS), caprylamidononanoyl oxybenzene sulphonate (NACA-OBS), 3,5,5-trimethyl hexanoyloxybenzene sulphonate (Iso-NOBS), dodecyl oxybenzene sulphonate (LOBS), and any mixture thereof; caprolactams; pentaacetate glucose (PAG); nitrile quaternary ammonium; imide bleach activators, such as N-nonanoyl-N-methyl acetamide; and any mixture thereof.

A suitable source of available oxygen (AvOx) is a source of hydrogen peroxide, such as percarbonate salts and/or perborate salts, such as sodium percarbonate. The source of peroxygen may be at least partially coated, or even completely coated, by a coating ingredient such as a carbonate salt, a sulphate salt, a silicate salt, borosilicate, or any mixture thereof, including mixed salts thereof. Suitable percarbonate salts can be prepared by a fluid bed process or by a crystallization process. Suitable perborate salts include sodium perborate mono-hydrate (PB1), sodium perborate tetra-hydrate (PB4), and anhydrous sodium perborate which is also known as fizzing sodium perborate. Other suitable sources of AvOx include persulphate, such as oxone. Another suitable source of AvOx is hydrogen peroxide.

A suitable pre-formed peracid is N,N-pthaloylamino peroxycaproic acid (PAP).

Suitable bleach catalysts include oxaziridinium-based bleach catalysts, transition metal bleach catalysts and bleaching enzymes.

A suitable oxaziridinium-based bleach catalyst has the formula:

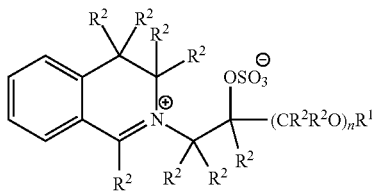

wherein: $R^1$ is selected from the group consisting of: H, a branched alkyl group containing from 3 to 24 carbons, and a linear alkyl group containing from 1 to 24 carbons; $R^1$ can be a branched alkyl group comprising from 6 to 18 carbons, or a linear alkyl group comprising from 5 to 18 carbons, $R^1$ can be selected from the group consisting of: 2-propylheptyl, 2-butyloctyl, 2-pentylnonyl, 2-hexyldecyl, n-hexyl, n-octyl, n-decyl, n-dodecyl, n-tetradecyl, n-hexadecyl, n-octadecyl, iso-nonyl, iso-decyl, iso-tridecyl and iso-pentadecyl; $R^2$ is independently selected from the group consisting of: H, a branched alkyl group comprising from 3 to 12 carbons, and a linear alkyl group comprising from 1 to 12 carbons; optionally $R^2$ is independently selected from H and methyl groups; and n is an integer from 0 to 1.

The composition may include transition metal bleach catalyst, typically comprising copper, iron, titanium, ruthenium, tungsten, molybdenum, and/or manganese cations. Suitable transition metal bleach catalysts are manganese-based transition metal bleach catalysts.

The composition may comprise a reducing bleach. However, the composition may be substantially free of reducing bleach; substantially free means "no deliberately added". Suitable reducing bleach include sodium sulphite and/or thiourea dioxide (TDO).

The composition may comprise a co-bleach particle. Typically, the co-bleach particle comprises a bleach activator and a source of peroxide. It may be highly suitable for a large amount of bleach activator relative to the source of hydrogen peroxide to be present in the co-bleach particle. The weight ratio of bleach activator to source of hydrogen peroxide present in the co-bleach particle can be at least 0.3:1, or at least 0.6:1, or at least 0.7:1, or at least 0.8:1, or at least 0.9:1, or at least 1.0:1.0, or even at least 1.2:1 or higher. The co-bleach particle can comprise: (i) bleach activator, such as TAED; and (ii) a source of hydrogen peroxide, such as sodium percarbonate. The bleach activator may at least partially, or even completely, enclose the source of hydrogen peroxide. The co-bleach particle may comprise a binder. Suitable binders are carboxylate polymers such as polyacrylate polymers, and/or surfactants including non-ionic detersive surfactants and/or anionic detersive surfactants such as linear $C_{11}$-$C_{13}$ alkyl benzene sulphonate. The co-bleach particle may comprise bleach catalyst, such as an oxaziridium-based bleach catalyst.

The composition of the present invention may also include photo bleaches and/or catylists. For example, U.S. Pat. No. 6,232,281; US 2005028294; US 2009285768; EP 2213947 and WO 2004105874 disclose examples thereof. Other examples may include a photoactive moiety such as one selected from the group consisting of 1,1'-biphenyl-4,4'-diamine, 1,1'-biphenyl-4-amine, benzophenone, 1,1'-biphenyl-4,4'-diol, 1,1'-biphenyl-4-amine, 1,1'-biphenyl-4-ol, 1,1':2',1"-terphenyl, 1,1':3',1"-terphenyl, 1,1': 4',1":4",1'''-quaterphenyl, 1,1': 4',1'''-terphenyl, 1,10-phenanthroline, 1,1'-biphenyl, 1,2,3,4-dibenzanthracene, 1,2-benzenedicarbonitrile, 1,3-isobenzofurandione, 1,4-naphthoquinone, 1,5-naphthalenediol, 10H-phenothiazine, 10H-phenoxazine, 10-methylacridone, 1-acetonaphthone, 1-chloroanthraquinone, 1-hydroxyanthraquinone, 1-naphthalenecarbonitrile, 1-naphthalenecarboxaldehyde, 1-naphthalenesulfonic acid, 1-naphthalenol, 2(1H)-quinolinone, 2,2'-biquinoline, 2,3-naphthalenediol, 2,6-dichlorobenzaldehyde, 21H,23H-porphine, 2-aminoanthraquinone, 2-benzoylthiophene, 2-chlorobenzaldehyde, 2-chlorothioxanthone, 2-ethylanthraquinone, 2H-1-benzopyran-2-one, 2-methoxythioxanthone, 2-methyl-1,4-naphthoquinone, 2-methyl-9(10-methyl)-acridinone, 2-methylanthraquinone, 2-methylbenzophenone, 2-naphthalenamine, 2-naphthalenecarboxylic acid, 2-naphthalenol, 2-nitro-9(10-methyl)-acridinone, 9(10-ethyl)-acridinone, 3,6-qcridinediamine, 3,9-dibromoperylene, 3,9-dicyanophenanthrene, 3-benzoylcoumarin, 3-methoxy-9-cyanophenanthrene, 3-methoxythioxanthone, 3'-methylacetophenone, 4,4'-dichlorobenzophenone, 4,4'-dimethoxybenzophenone, 4-bromobenzophenone, 4-chlorobenzophenone, 4'-fluoroacetophenone, 4-methoxybenzophenone, 4'-methylacetophenone, 4-methylbenzaldehyde, 4-methylbenzophenone, 4-phenylbenzophenone, 6-methylchromanone, 7-(diethylamino)coumarin, 7H-benz[de]anthracen-7-one, 7H-benzo[c]xanthen-7-one, 7H-furo[3,2-g][1]benzopyran-7-one, 9(10H)-acridinone, 9(10H)-anthracenone, 9(10-methyl)-acridinone, 9 (10-phenyl)-acridinon, 9,10-anthracenedione, 9-acridinamine, 9-cyanophenanthrene, 9-fluorenone, 9H-carbazole, 9H-fluoren-2-amine, 9H-fluorene, 9H-thioxanthen-9-ol, 9H-thioxanthen-9-one, 9H-thioxanthene-2,9-diol, 9H-xanthen-9-one, acetophenone, acridene, acridine, acridone, anthracene, anthraquinone, anthrone, a-tetralone, benz[a]anthracene, benzaldehyde, benzamide, benzo[a]coronene, benzo[a]pyrene, benzo[f]quinoline, benzo[ghi]perylene, benzo[rst]pentaphene, benzophenone, benzoquinone, 2,3,5,6-tetramethyl, chrysene, coronene, dibenz[a,h]anthracene, dibenzo[b,def]chrysene, dibenzo[c,g]phenanthrene, dibenzo[def,mno]chrysene, dibenzo[def,p]chrysene, DL-tryptophan, fluoranthene, fluoren-9-one, fluorenone, isoquinoline, methoxycoumarin, methylacridone, michler's ketone, naphthacene, naphtho[1,2-g]chrysene, N-methylacridone, p-benzoquinone, p-benzoquinone, 2,3,5,6-tetrachloro, pentacene, phenanthrene, phenanthrenequinone, phenanthridine, phenanthro[3,4-c]phenanthrene, phenazine, phenothiazine, p-methoxyacetophenone, pyranthrene, pyrene, quinoline, quinoxaline, riboflavin 5'-(dihydrogen phosphate), thioxanthone, thymidine, xanthen-9-one, xanthone, derivatives thereof, and mixtures thereof.

Preferably, the photoactive moiety is selected from the group consisting of xanthone, xanthene, thioxanthone, thioxanthene, phenothiazine, fluorescein, benzophenone, alloxazine, isoalloxazine, flavin, derivatives thereof, and mixtures thereof. In one preferred embodiment, the photoactive moiety is thioxanthone.

Other suitable water-soluble photoactivators for the consumer product compositions of the present invention include fluoresceins and derivatives thereof; preferably halogen substituted fluoresceins; more preferably bromo- and iodo-fluoresceins such as dibromo fluorescein, diodo fluorescein, rose bengal, erythrosine, eosin (e.g. Eosin Y).

Color Restoration:

The method and device of the present invention may also be used to restore colors to surfaces such as fabrics and hard surfaces. Examples of compositions that can be used for color restoration include those set forth in the following patents as US 200924562; WO 2010025097; US 20080242584; US 20110177994; US 2008/0242584A1; U.S. Ser. No. 00/906,906; US 200906907; US 2009088363; US 2009209445; U.S. Pat. Nos. 8,003,589; 8,188,026; 8,236,745; 8,357,648; US 2009249562; U.S. Pat. No. 8,097,047; US 2012246840; US 200917811; US 200917812; WO 8084460; WO 8084461; US 2010056419; US 201005642; US 2010056421; US 201129661; U.S. Pat. Nos. 8,193,141; 8,372,795; 8,193,141; 8,969,281, and in the example, below.

disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

| | Example (% active) | | | | | | | | | | |
|---|---|---|---|---|---|---|---|---|---|---|---|
| Component Material | I | II | III | IV | V | VI | VII | VIII | IX | X | XI |
| AE3S NH4[1] | 2.0 | — | 3.0 | — | — | — | — | — | — | — | 2.0 |
| AE 1.8S[2] | — | 5.0 | — | 3.0 | 2.0 | — | — | — | 5.0 | — | — |
| HLAS[3] | — | — | — | — | — | 3.0 | 5.0 | 7.0 | — | — | — |
| Surfonic 24-9[4] | 3.0 | 5.0 | 2.0 | 5.0 | 4.0 | 10.0 | 12.0 | 15.0 | 7.0 | — | 1.0 |
| Merquat ® 100[5] | — | — | 3.0 | 3.0 | — | 6.0 | — | 3.0 | 3.0 | 6.0 | 2.0 |
| Merquat ® 106[6] | 3.5 | 3.5 | — | — | — | — | — | — | — | — | — |
| Merquat ® 280[7] | — | — | — | — | 5.0 | — | 5.0 | — | — | — | — |
| Betaine[8] | 7.0 | 5.0 | 7.0 | 8.0 | 3.0 | 5.0 | 5.0 | 7.0 | 8.0 | 7.5 | 7.0 |
| TAE80[9] | — | — | — | — | — | 2 | — | — | — | — | 1 |
| Water | Balance to 100% | | | | | | | | | | |

[1]Alkyl ethoxylate sulfate, 3 moles of ethoxylation, available from The Procter & Gamble Company.
[2]Alkyl ethoxylate, available from The Procter & Gamble Company.
[3]Linear alkylbenzene sulfonate, available from The Procter & Gamble Company.
[4]Nonionic surfactant, available from Huntsman Corp.
[5]Homopolymer of diallyldimethyl ammonium chloride, polymer molecular weight of from about 100,000 to about 150,000.
[6]Homopolymer of diallyldimethyl ammonium chloride, polymer molecular weight from about 5,000 to about 15,000.
[7]Co-polymer of dimethyldiallyl ammonium chloride and acrylic acid, molecular weight of about 450,000 to 550,000 Daltons.
[8]Lauryl amido propyl betaines, or C12-C16 cocoamido propyl betaines (supplied from Inolex under the tradename Lexaine ® CG30).
[9]Dispersing agent, ethoxylated tallow amine, available from BASF.

Protecting Surfaces:

The method and device of the present invention may be used to apply compositions that can protect surfaces. For example, a composition may be applied that protects fibrous materials from damage, that protects printed designs, that modifies the surface to make it water resistant or more hydrophilic. The composition can also provide a protective covering on solid surfaces such as stone, concrete, plastic, wood, etc. to help prevent water damage, staining, damage from objects hitting the surface, light, and chemicals, etc. Materials suitable for use as protectants include, but are not limited to, oils, Teflon coating materials, silicone, dusting material, waxes, polymers, epoxy materials, UV blockers, film producing materials and combinations of these and other materials known or found to protect surfaces.

Other Uses:

The method and device of the present invention can be used to apply other types of compositions to treat hard and flexible surfaces. For example, the following patents disclose compositions that can be used to help cleaning, help provide desirable characteristics to fabrics and other surfaces, and to help conserve material and energy when washing or otherwise treating fabrics: U.S. Pat. No. 6,503,413; US 2005/060811; and US 2005/098759.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of depositing a composition comprising antibacterial agents on a hard surface, the method comprising the steps of:
    identifying the hard surface onto which the composition will be deposited;
    providing a device having a sensor, a reservoir for the composition, a CPU, and at least one microfluidic die comprising at least one nozzle;
    locating the sensor over at least a portion of the hard surface;
    activating the sensor to sense bacteria on the hard surface;
    providing acquired information on the bacteria to the CPU;
    instructing the CPU to calculate the location of the bacteria on the hard surface; and
    activating the at least one nozzle to deposit the composition on the hard surface at the location of the bacteria.

2. The method of claim 1, including the additional step of sensing the hard surface after the compostions has been deposited thereon.

3. The method of claim 1, wherein the microfluidic die includes a plurality of nozzles.

4. The method of claim 1, wherein the microfluidic die includes a heating element or an electromechanical actuator.

5. The method of claim 1, wherein the CPU is configured to activate the one or more nozzles in a discontinuous deposition pattern.

6. The method of claim 1, wherein the CPU is configured to activate the one or more nozzles in a continuous deposition pattern.

7. The method of claim 1, wherein the number and or frequency of nozzles fired can be adjusted by a user of the device.

8. The method of claim 1 where the one or more nozzles are disposed in an array that is a linear configuration, multiple rows, off-set, sine wave, curved, circular, or saw tooth arrangements.

9. The method of claim 1, wherein the device further comprises an illumination source configured to illuminate the surface to be sensed.

10. The method of claim 1, wherein the sensor utilizes color, brightness, reflectance, refractance temperature, texture, depth, width, length, odor, and mixtures thereof.

* * * * *